United States Patent [19]

Coles et al.

[11] Patent Number: 5,427,740
[45] Date of Patent: Jun. 27, 1995

[54] TIN OXIDE GAS SENSORS

[75] Inventors: Gary S. V. Coles, Swansea; Geraint Williams, Dyfed; Brian M. Smith, Swansea, all of United Kingdom

[73] Assignee: British Gas PLC, London, England

[21] Appl. No.: 129,085
[22] PCT Filed: Apr. 3, 1992
[86] PCT No.: PCT/GB92/00604
 § 371 Date: Oct. 7, 1993
 § 102(e) Date: Oct. 7, 1993
[87] PCT Pub. No.: WO92/17773
 PCT Pub. Date: Oct. 15, 1992

[30] Foreign Application Priority Data

Apr. 5, 1991 [GB] United Kingdom ............ 9107216
Apr. 5, 1991 [GB] United Kingdom ............ 9107228

[51] Int. Cl.$^6$ ............................................. G01N 27/12
[52] U.S. Cl. ........................................ 422/83; 422/94; 422/98; 436/144; 436/127; 436/138; 73/335.05; 419/19; 437/188; 437/205
[58] Field of Search ........................ 422/83, 98, 94; 436/139, 127, 144; 73/335.05, 31.06; 419/19; 338/34; 437/205, 188

[56] References Cited

U.S. PATENT DOCUMENTS

| | | | |
|---|---|---|---|
| 4,030,340 | 6/1977 | Chang | 73/23 |
| 4,542,640 | 9/1985 | Clifford | 73/23 |
| 4,614,669 | 9/1986 | Yannopoulos | 427/87 |
| 4,688,014 | 8/1987 | Kitaguchi | 338/34 |
| 4,701,739 | 10/1987 | Sasaki | 338/34 |
| 4,775,412 | 10/1988 | Nishikura et al. | 75/0.5 A |
| 4,911,892 | 3/1990 | Grace et al. | 422/94 |

FOREIGN PATENT DOCUMENTS

| | | |
|---|---|---|
| 0114310 | 8/1984 | European Pat. Off. . |
| 0141090 | 5/1985 | European Pat. Off. . |
| 0147213 | 7/1985 | European Pat. Off. . |
| 0157328 | 10/1985 | European Pat. Off. . |
| 0206839 | 12/1986 | European Pat. Off. . |
| 0261275 | 3/1988 | European Pat. Off. . |
| 0280540 | 8/1988 | European Pat. Off. . |
| 0375013 | 6/1990 | European Pat. Off. . |
| 1280809 | 7/1972 | United Kingdom . |
| 1282993 | 7/1972 | United Kingdom . |
| 1288009 | 9/1972 | United Kingdom . |
| 1596095 | 8/1981 | United Kingdom . |
| 2149123 | 6/1985 | United Kingdom . |
| 2177215 | 1/1987 | United Kingdom . |
| 9114939 | 3/1991 | WIPO . |
| WO91/14939 | 10/1991 | WIPO . |

OTHER PUBLICATIONS

J. Watson, "The Tin Oxide Gas Sensor and Its Applications," Sensors and Actuators, 5 (1984), pp. 29–42.

(List continued on next page.)

*Primary Examiner*—Timothy M. McMahon
*Assistant Examiner*—N. Bhat
*Attorney, Agent, or Firm*—William R. Hinds

[57] ABSTRACT

Tin oxide sensors are made by mixing antimony bearing material with tin oxide powder and formation of the sensor by deposition of a slurry of the mixture onto a substrate and drying and sintering the slurry, the antimony bearing material being present in an amount sufficient to render the sensitivity of the sensor to one or more of the gases $H_2$, CO, or $CH_4$, relatively independent of the concentration of oxygen in the range $P_{O2}$ $10^{-1}$–1 atm. A further type of a tin oxide gas sensor is disclosed having a resistivity that at a measuring temperature increases with concentration of at least one gas to be measured, the sensor is made by calcining the tin oxide in air at a temperature in excess of 1400° C., or otherwise treating the tin oxide so that it has a state of physical aggregation consistent with being formed in such manner. At a second measuring temperature the resistivity of the sensor to said one gas decreases with increasing gas concentration. The resistivity of the sensor is dependent on the concentration of several gases, the dependence at differing measuring temperatures being such that by measuring the resistivity of the sensor at several different measuring temperatures the composition of a gas to which the sensor is exposed may be calculated. An array of such tin oxide gas sensors may be mounted on a single substrate having heater means to maintain the sensors at differing temperatures. Such an array may also include an antimony bearing sensor as disclosed or other tin oxide sensors.

13 Claims, 10 Drawing Sheets

OTHER PUBLICATIONS

Kousuke Ihokura, "Tin Oxide Gas Sensor for Deoxidizing Gas," New Materials & New Processes, vol. 1, 1981, pp. 43–50.

Henry Windischmann and Peter Mark, "A model for the Operation of a Thin-Film $SnO_x$ Conductance-Modulation Carbon Monoxide Sensor," J. Electrochem. Soc., vol. 126, No. 4, pp. 627–633.

G. Heiland, "Homogenous Semiconducting Gas Sensors," Sensors and Actuators, 2 (1982), pp. 343–361.

M. Nitta and M. Haradome, "CO Gas Detection by $ThO_2$–Doped $SnO_2$," Journal of Electronic Materials, vol. 8, No. 5, 1979, pp. 571–580.

J. F. Goodman and S. J. Gregg, "The Production of Active Solids by Thermal Decomposition. Part XI. The Heat Treatment of Precipitated Stannic Oxide," J. Chem. Soc., 1960, pp. 1162–1167.

S. Yasunaga, S. Sunahara and K. Ihokura, "Effects of Tetraethyl Orthosilicate Binder on the Characteristics of an $SnO_2$ Ceramic–Type Semiconductor Gas Sensor," Sensors and Actuators, 9 (1968), pp. 133–145.

E. Bornand, "Influence of the Annealing Temperature of Non-Doped Sintered Tin Dioxide Sensors on Their Sensitivity and Response Time to Carbon Monoxide," Sensors and Actuators, 4 (1983), pp. 613–620.

G. S. V. Coles, G. Williams and B. Smith, "Selectivity Studies on Tin Oxide–Based Semiconductor Gas Sensors," Sensors and Actuators B, 3(1991), pp. 7–14.

Jerome F. McAleer, Patrick T. Moseley, John O. W. Norris and David E. Williams, "Tin Dioxide Gas Sensors," J. Chem. Soc., Faraday Trans. 1, 1987, 83, pp. 1323–1346.

G. S. V. Coles, G. Williams and B. Smith, "The Effect of Oxygen Partial Pressure on the Response of Tin (IV) Oxide Based Gas Sensors," J. Phys. D; Appl. Phys., 24 (1991), pp. 633–641.

Shih–Chia Chang, "Oxygen Chemisorption of Tin Oxide: Correlation Between Electrical Conductivity and EPR Measurements," J. Vac. Sci. Technol., 17(1), Jan.-/Feb. 1980, pp. 366–369.

S. Novel, C. Pijolat, R. Lalauze, M. Loesch and L. Combes, "Influence of Grain Size and Working Temperature on the Performances of a Sensor Produced from Polyicrystalline Tin Dioxide", article presented at the Sensors and Their Applications IV Conference, Canterbury, 1989.

P. K. Clifford and D. T. Tuma, "Characteristics of Semiconductor Gas Sensors I. Steady State Gas Response," Sensors and Actuators, 3 (1982/83), pp. 233–254.

Shinji Kanefusa, Masayoshi Nitta, and Miyoshi Haradome, "Some Unique Aspects on $ThO_2$–Doped $SnO_2$ Exposed to $H_2$ Gas," J. Appl. Phys. 50(2), Feb. 1979, pp. 1145–1146.

Shinji Kanefusa, and Miyoshi Haradome, "Unique Phenomena in $SnO_2$–Based Gas Sensing Devices Exposed to Ammonia Gas," Solid State Electronics, vol. 27, No. 6, 1984, pp. 533–536.

M. J. Fuller and M. E. Warwick, "The Catalytic Oxidation of Carbon Monoxide on Tin(IV) Oxide," Journal of Catalysis 29, (1973), pp. 441–450.

Masayoshi Itoh, Hideshi Hattori, and Kozo Tanabe, "Catalytic Sites on $SnO_2$ and $TiO_2$–$SnO_2$ for the Isomerization of 1–Butene," Journal of Catalysis 43 (1976), pp. 192–199.

N. Murakami, K. Tanaka, K. Sasaki, and K. Ihokura, "The Influence of Sintering Temperature on the Characteristics of $SnO_2$ Combustion Monitor Sensors," pp. 165–170, 1983, Ann. Chem. Symp. Ser., 17.

J. G. Firth, A. Jones, and T. A. Jones, "Solid State Detectors for Carbon Monoxide," pp. 63–68, 1975, Ann. occup. Hyg., vol. 18.

N. Yamazoe, Y. Kurokawa, and T. Seiyama, "Hydrogen Sensitive Gas Detector Using Silver Added Tin-(IV)Oxide", pp. 1899–1902, 1982, The Chemical Society of Japan.

Colin A. Vincent, "The Nature of Semiconductivity in Polycrystalline Tin Oxide," 515–521, 1972, J. Electrochem. Soc.: Solid-State Science and Technology.

Keizo Uematsu, Nobuyasu Mizutani, Masanori Kato, "Electrical Properties of High Purity Tin Dioxide Doped with Antimony," 1987, pp. 915–918, Journal of Materials Science, 22.

David E. Williams and Patrick T. Moseley, "Dopant Effects on the Response of Gas-sensitive Resistors Utilising Semiconducting Oxides," pp. 809–814, 1991, J. Mater. Chem, 1(5).

G. N. Advani, Y. Komem, J. Hasenkopf, A. G. Jordan, "Improved Performance of $SnO_2$ Thin–Film Gas Sensors Due to Gold Diffusion," pp. 139–147, 1981, Sensors and Actuators, 2.

(List continued on next page.)

OTHER PUBLICATIONS

N. Yamazoe, Y. Kurokawa and T. Seiyama, "Effects of Additives on Semiconductor Gas Sensors," pp. 283–289, 1983, Sensors and Actuators, 4.

K. Ihokura, K. Tanaka and N. Murakami, "Use of Thin Dioxide Sensor to Control a Domestic Gas Heater," pp. 607–612, 1983, Sensors and Actuators, 4.

D. Baresel, W. Gellert, W. Sarholz and P. Scharner, "Influence of Catalytic Activity on Semiconducting Metal Oxide Sensors," pp. 35–50, 1984, Sensors and Actuators, 6.

G. S. V. Coles and K. J. Gallagher, "Fabrication and Preliminary Tests on Tin (IV) Oxide–Based Gas Sensors," pp. 89–96, 1985, Sensors and Actuators, 7.

L. N. Yannopoulos, "Antimony–Doped Stannic Oxide–Based Thick–Film Gas Sensors," pp. 77–89, 1987, Sensors and Actuators, 12.

H. Torvela, P. Romppainen and S. Leppavuori, "Detection of CO Levels in Combustion Gases by Thick–Film $SnO_2$ Sensor," pp. 19–25, 1988, Sensors and Actuators, 14.

"Tin Dioxide Gas Sensors for the Detection of Organic Vapours," 1986, Technical Information Leaflet, Health and Safety Executive, Research and Laboratory Services Division.

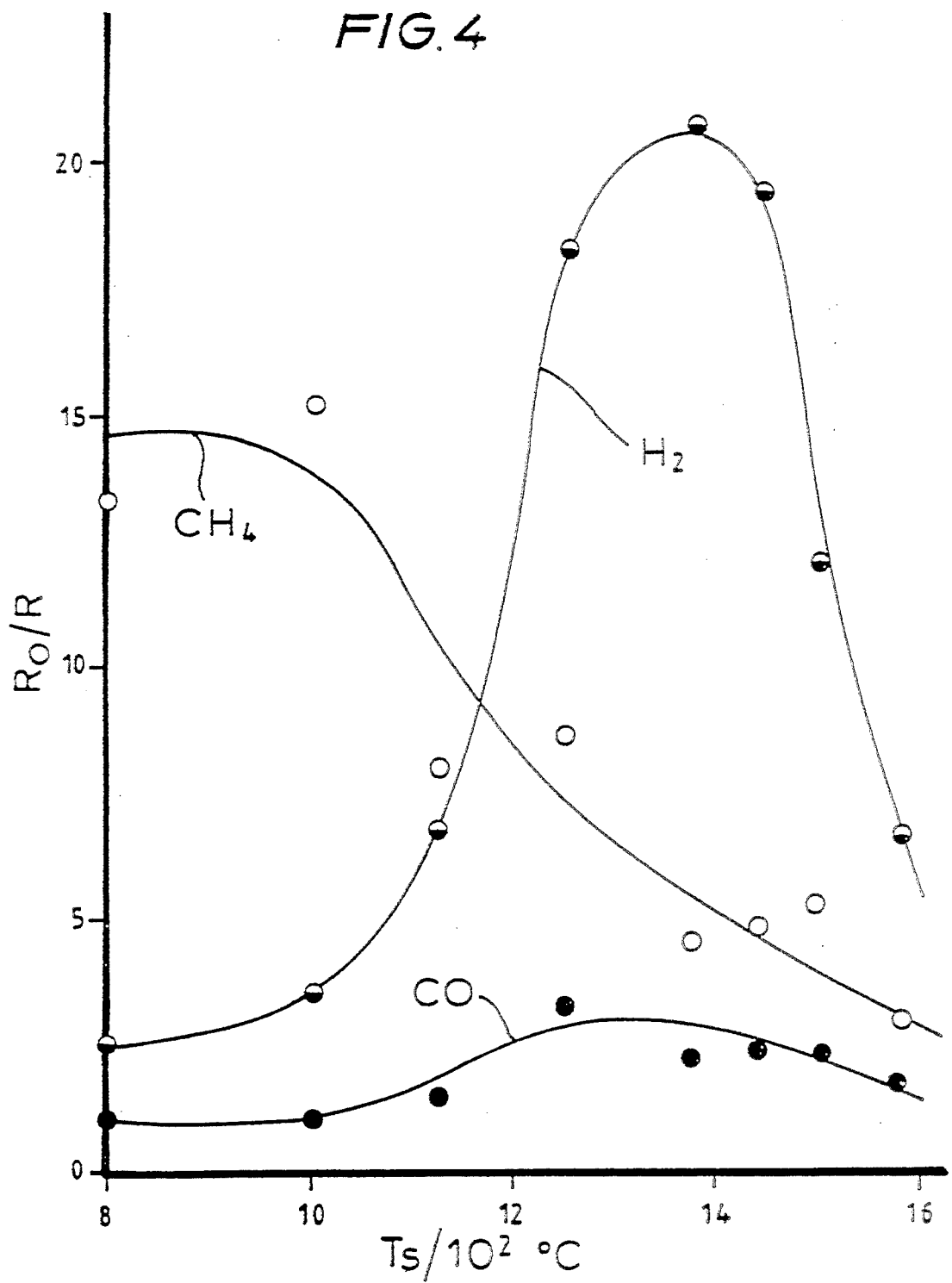

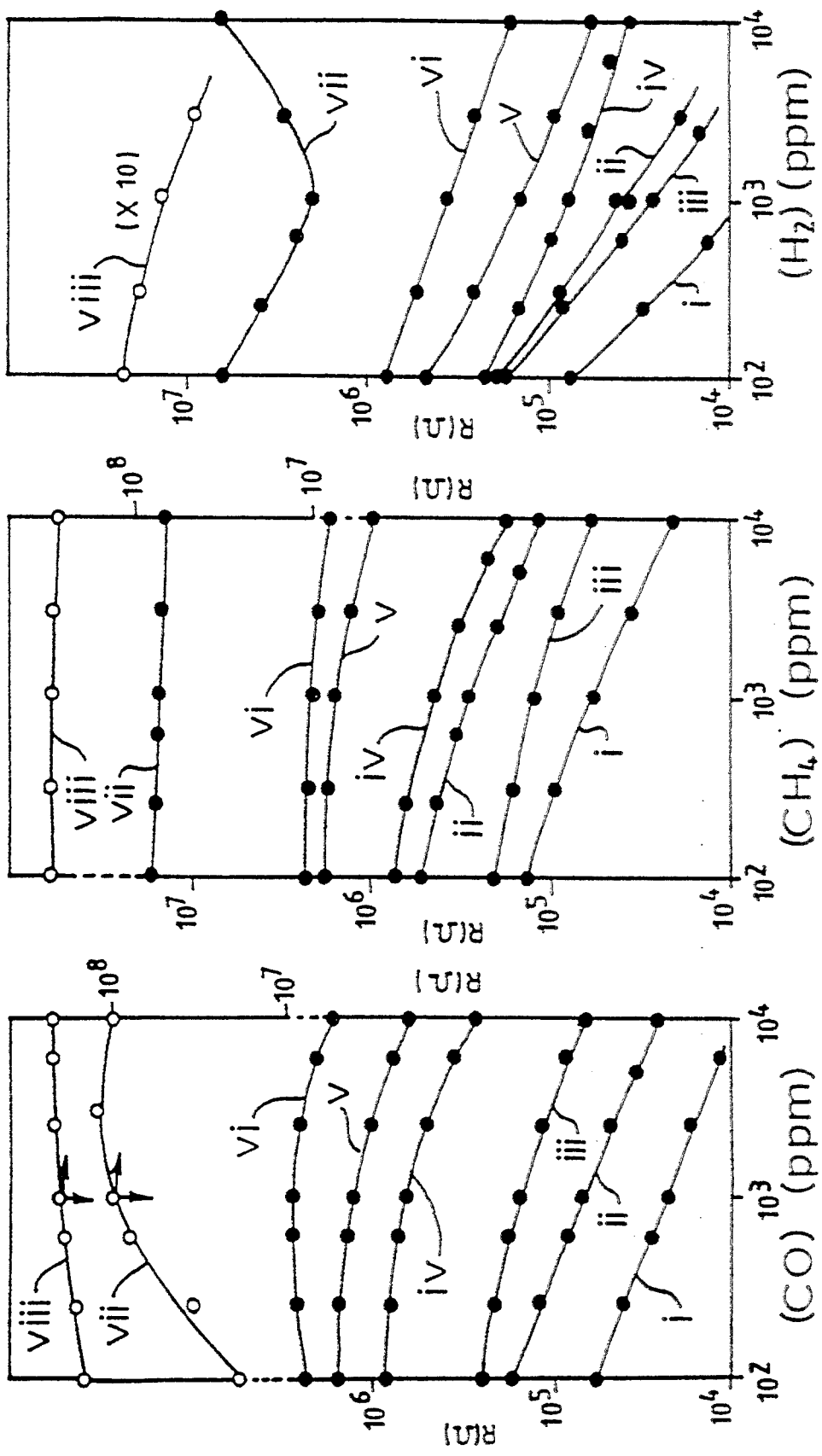

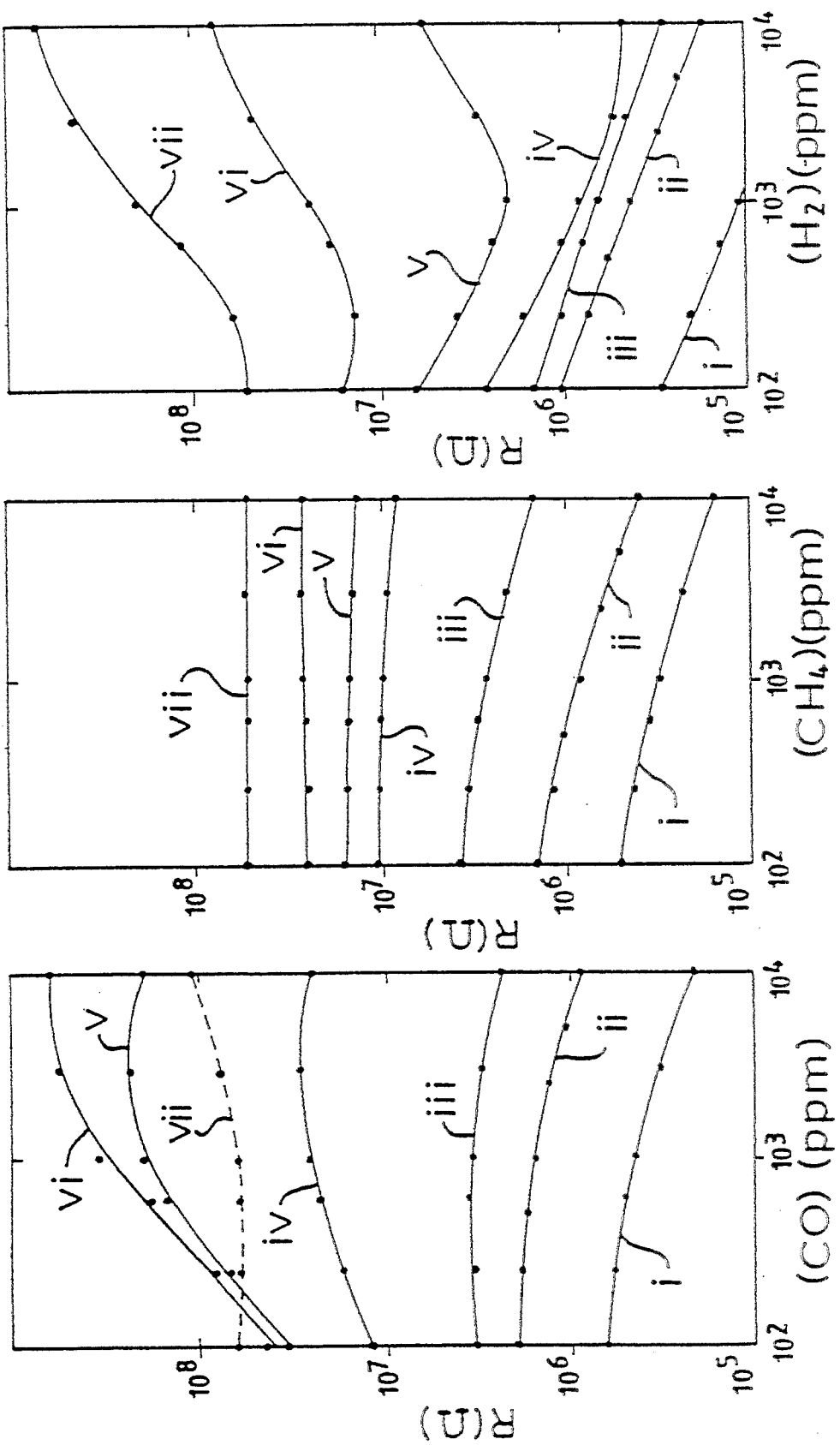

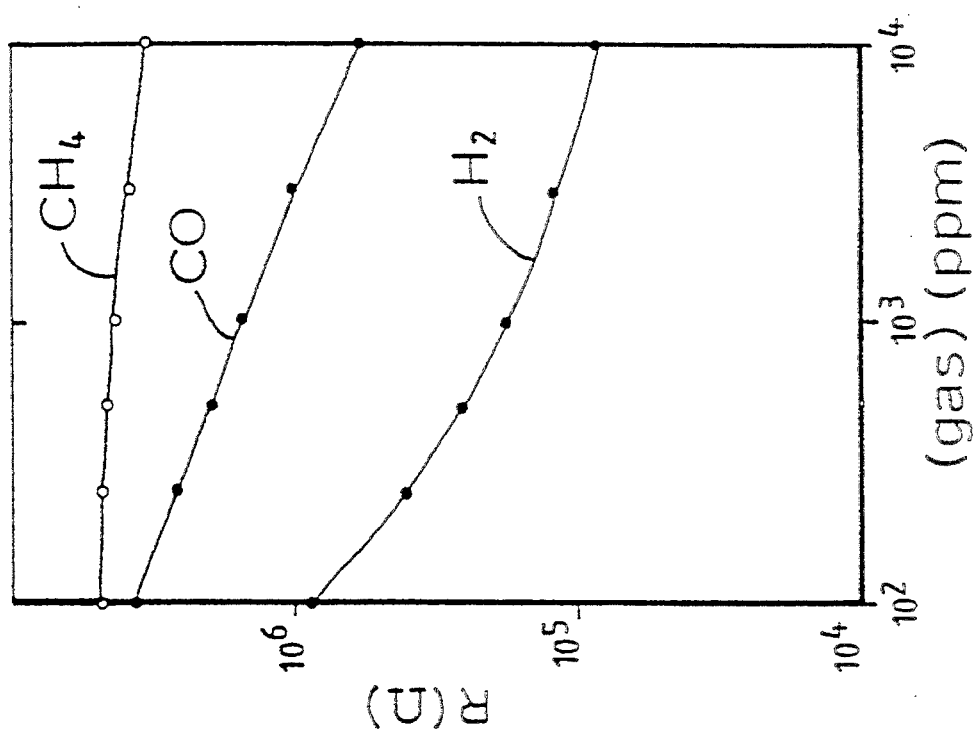
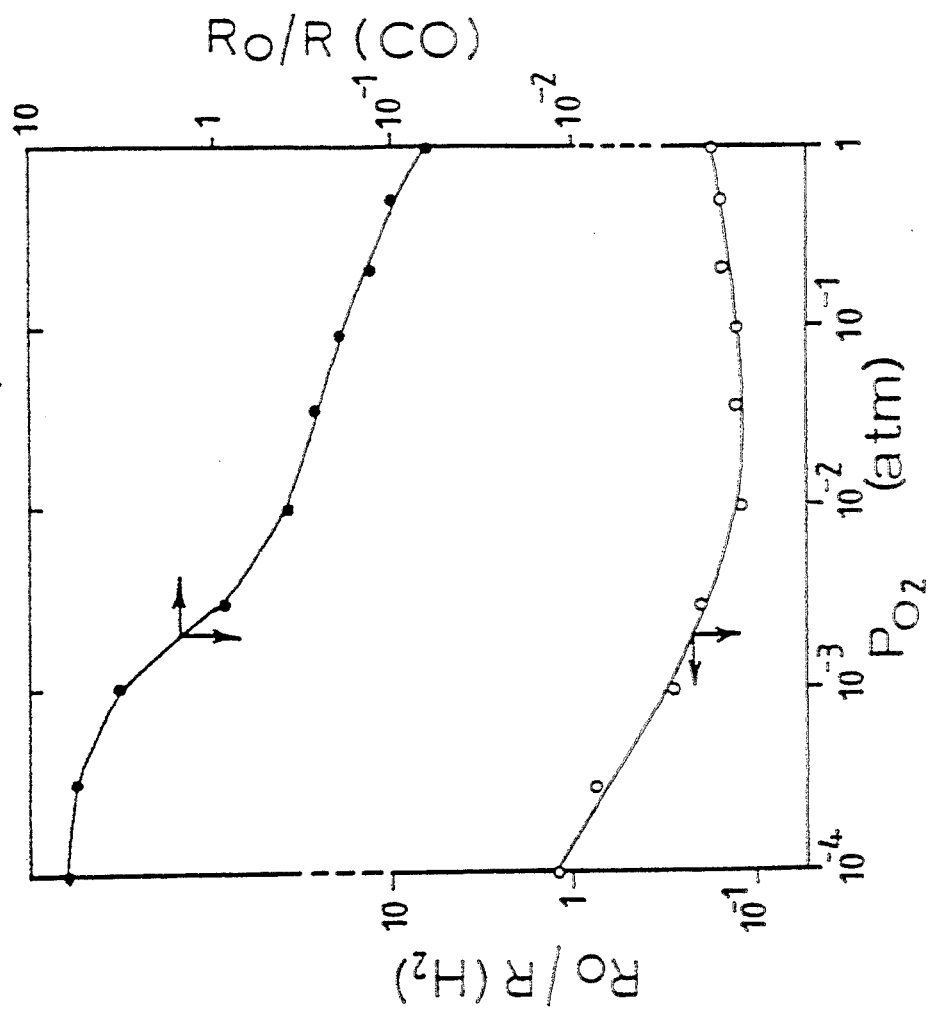
FIG. 8
FIG. 8(b)

TIN OXIDE GAS SENSORS

This invention relates to gas sensors of the type in which the resistance, or other electrical property, of a sample of tin (IV) oxide ($SnO_2$) is measured, the resistance, or other electrical property, being dependent on the concentration of the gas in the surrounding medium. In the following reference is made to measurement of resistivity but it should be understood that the invention is not restricted to such measurement. At the rear of this description is a list of prior art relating to tin oxide sensors and reference numerals in the description refers to this list of prior art.

Tin (IV) oxide ($SnO_2$) is widely used as the basis of solid state sensors capable of detecting a variety of toxic and flammable gases [1-7]. Tin (IV) oxide is an n-type semiconductor in which electrical conductivity occurs through negative charge carriers.

The active sensing element usually consists of a sintered polycrystalline mass of the oxide as exemplified by the many forms of the Figaro gas sensor produced in Japan. The fabrication procedure adopted involved heat treatment of the $SnO_2$ along with any other additives such as $PdCl_2$ or $ThO_2$ [2, 5, 6], which are initially dispersed in an aqueous slurry. This sintering process yields a sensor body of suitable mechanical strength and also confers thermal stability, which is essential considering the elevated temperatures (300° C.–400° C.) at which these devices are operated. In order to achieve the desired thermal stability, the sintering temperature ($T_S$) used must be significantly higher than the sensor operating temperature ($T_o$). Typical values of $T_S$ quoted in the literature for commercially available devices lie in the range 500°–700° C. [2, 6, 7]. However, it is widely known that tin oxide alone sinters poorly at these temperatures. Values of $T_S$ exceeding 1100° C., which marks the Tamman temperature of the material [8], are required to achieve accelerated adhesion between neighbouring crystallites. To improve low temperature inter-granular cementing, binders such as tetraethyl ortho-silicate (TEOS) [9], MgO [6] or alumina [10] are often incorporated prior to heat treatment. These binders may significantly alter the gas sensing characteristics of the material, for example, in the case of TEOS, which decomposes at elevated temperatures forming Si—O bridges between the $SnO_2$ grains, the presence of the binder confers a marked increase in sensitivity to flammable gases [9].

Considering the importance of the heat treatment step in the overall fabrication procedure, comparatively few studies have been performed on the influence of sintering temperature on the characteristics of $SnO_2$ based gas sensors. Research carried out by Borand [11] on pressed pellets of polycrystalline $SnO_2$ annealed in the 400° C.–900° C. range showed that maximum CO sensitivity along with the shortest response time occurred at a sintering temperature of 700° C. However, for a tin oxide combustion monitoring device Sasaki and his co-workers [12] found that a sintering temperature of 1300° C. gave the most desirable characteristics.

Such sensors have been widely described and are usually in the form of a thin or thick film deposit of the tin oxide on an alumina or other insulating ceramic substrate. Platinum paste contacts are used to connect the tin oxide to wires for resistance measurement and an electrical resistance heating element may be provided on the substrate.

Tin oxide sensors suffer a major drawback in that they are sensitive to many gases and worse there are also some cross-sensitivities, i.e. the presence of one gas will alter the sensitivity of the sensor to the presence of a second gas.

A notable cross-sensitivity is the influence of oxygen at low oxygen partial pressures. It is found that an undoped $SnO_2$ sensor experiences large changes in resistance (greater than three orders of magnitude) upon exposure to gases such as CO or $H_2$ under conditions of reduced oxygen partial pressure.

A further problem in the manufacture of such tin oxide gas sensor is controlling the resistivity of the sensor so as to be readily measurable. It is well-known to add antimony oxide ($Sb_2O_3$) as an aid to reducing the base resistance of the tin oxide sensor. In a paper in Sensors and Actuators 12 (1987) pages 77-89 [15], L. N. Yannopoulos described the use of $Sn_{0.98}Sb_{0.02}O_2$. These researches indicated (pages 86, 87) that the gas sensor response to $H_2$ was affected by changes in the partial pressure of oxygen over the range 0.25–2.0%.

European Patent specification No. 0147213 (Westinghouse Electric Corporation) discloses antimony doped tin oxide sensors containing 0.5–2.5% w/w antimony formed by co-precipitation of tin and antimony mixed hydroxide from an admixture of stannic chloride liquid and antimony pentachloride liquid. The sensors produced were suitable for detection of CO and $H_2$ but showed a marked oxygen cross-sensitivity (see FIGS. 4 & 5).

United Kingdom 1596095 discloses use of antimony at a very low level (<0.1% w/w) and is directed to use of such sensors as gas alarms and does not address the problem of oxygen sensitivity at low oxygen partial pressures.

European No. 0114310 discloses use of antimony and platinum in a tin oxide sensor, the ratio of antimony to tin being 2:8 mole % and the ratio of platinum to tin being in the ratio of 2:10 mole %. This specification discloses very high levels of platinum and makes no mention of the suppression of of oxygen dependence. The main difference between this sensor and other sensors is that it is worked at room temperature and so has a very long response time. The reason why the antimony and platinum was added was probably so as to obtain a resistance which is low enough to measure at ambient temperatures. A big problem with room-temperature sensors is that they tend to be more affected by changing humidity than gas composition. Further the process for forming the disclosed sensor involves firing at a temperature in the range 600°–850° C.

European Patent Specification No. 0261275 is to a hydrogen sensor using antimony in the ratio 0:8 mole % but gives no mention whatsoever of performance of the sensor in oxygen deficient conditions. The disclosed method is similar to that in European 0114310.

European 0280540 is to a sensor comprising an antimony doped tin oxide sensing medium with a filter to vary the performance of the sensor.

As will be clear from the above there are many workers in the field of tin oxide gas sensors yet none have appreciated the virtues of the present invention.

Tin oxide sensors generally decrease in resistivity when the concentration of the gas they are sensitive to increases. Exceptionally sensors of particular composition have been described which increase in resistivity as the concentration of a particular gas increases (see for example references 22, 23 listed below).

Two of the inventors in the present application have also developed and disclosed a linear-response hydrogen-selective tin oxide gas sensor incorporating bismuth (WO91/14939).

It has been proposed in U.S. Pat. No. 4,542,640 (Clifford) to provide a gas detection system incorporating several separate semiconductor gas sensors having different characteristics and processor means to produce an indication of gas concentration.

In a first aspect of the invention the inventors have found that by pre-calcining the tin oxide in such sensors they can control the behaviour of the sensor such that a sensor is obtained having widely different characteristics at different operating temperatures. Such a sensor can be used at several different temperatures and the results compared to obtain more accurate measurement of gas concentrations and composition than hitherto.

Alternatively several such sensors can be maintained at different temperatures so that their resistances can be measured simultaneously in a like manner to the U.S. Patent mentioned above.

Accordingly in a first aspect the present invention provides a tin oxide gas sensor having a resistivity that at a measuring temperature increases with concentration of at least one gas to be measured, the sensor being formed by calcining the tin oxide in air at a temperature in excess of 1400° C., or having a state of physical aggregation consistent with being formed in such manner.

The inventors believe that calcining at such temperatures alters the nature of the non-stoichiometry of the tin oxide, or possibly acts by other means affecting the state of physical aggregation of the tin oxide such as affecting the surface of the tin oxide particles. The inventors believe that such alteration in the nature of the non-stoichiometry or state of physical aggregation of the tin oxide may be creatable by other means such as firing in atmospheres with differing oxygen contents from air or by the use of reducing agents such as tin.

The invention further provides a method for making the resistivity of a tin oxide gas sensor at a measuring temperature increase with increase in the concentration of at least one gas to be measured by inducing in the tin oxide non-stoichiometry or a state of physical aggregation consistent with being formed by calcining the tin oxide in air at a temperature in excess of 1400° C.

Advantageously the calcining temperature is approximately 1500° C.

More advantageously, at a second measuring temperature the resistivity of the sensor to said one gas decreases with increasing gas concentration.

Yet more advantageously the resistivity of the sensor is dependent on the concentration of several gases, the dependence at differing measuring temperatures being such that by measuring the resistivity of the sensor at several different measuring temperatures the composition of a gas to which the sensor is exposed may be calculated.

In a further aspect of the invention the inventors have found that the susceptibility of tin oxide sensors to oxygen cross-sensitivity is depressed if certain dopants are used to lower the initial base resistance of the sensors.

The present applicants have found that if Sb(III) is included as a dopant the sensitivity to oxygen concentration decreases dramatically. When such a sensor incorporating, say, 2% $Sb_2O_3$, is exposed to conditions of reduced oxygen partial pressure ($P_{O2}$ in the range $10^{-4}$–1 atm.) the sensitivity to these gases merely increases by up to a factor of times two and usually much less. The inventors initially surmised that the antimony worked by reducing base resistance of the sensor, however comparative tests with other potential dopants. indicates that this is not the only mechanism operating.

Accordingly in a further aspect the present invention provides a method for the production of tin oxide sensors comprising the incorporation of antimony in the tin oxide in an amount sufficient to render the sensitivity of the sensor to one or more of the gases $H_2$, CO, or $CH_4$, relatively independent of the concentration of oxygen in the range $P_{O2}$ $10^{-4}$–1 atm.

Advantageously the concentration of antimony expressed as antimony oxide in the tin oxide is of the order of 2% w/w.

In yet a further aspect the invention provides a unitary sensor comprising a plurality of tin oxide sensors on a common substrate at least one of the sensors being an antimony doped sensor as described above and at least one other of the sensors being a high temperature calcined or like sensor as described above.

BRIEF DESCRIPTION OF THE DRAWINGS

Further features of the invention are exemplified by the following description and claims, with reference to the drawings in which FIGS. 1–9 refer to the investigation of non-stoichometry consistent with high temperature calcining and FIGS. 10–13 refer to investigation of suppression of oxygen cross-sensitivity:

FIG. 4: A plot of $R_o/R$ (where $R_o$=sensor resistance in air and R = resistance in a 1% v/v contaminant gas-/air mixture) versus sintering temperature ($T_S$) for a series of sensors maintained at $T_o$=400° C.

FIG. 5: As FIG. 3 except that a working temperature of 280° C. was employed. The reducing gases tested were (a) CO, (b) $CH_4$ and (c) $H_2$.

FIG. 6: Logarithmic plots of resistance response to reducing gas inclusions for a sensor prepared from $SnO_2$ sintered at 1500° C., and maintained at working temperatures of (i) 450° C., (ii) 400° C., (iii) 360° C., (iv) 320° C., (v) 280° C., (vi) 230° C. and (vii) 175° C. The contaminant gases used in each case are (a) CO, (b) $CH_4$ and (c) $H_2$.

FIG. 8a: A plot of sensor response (represented by the ratio of resistance in supporting gas to the resistance exhibited in the presence of a 1% v/v reducing gas inclusion) versus oxygen partial pressure for an undoped $SnO_2$ sample sintered at 1500° C. upon exposure to (i) CO at 280° C. and (ii) $H_2$ at 175° C.

FIG. 8(b): Sensor resistance response to reducing gas inclusions when the oxygen partial pressure in the base gas is fixed at $10^{-4}$ atm. An operating temperature of 280° C. was employed.

INVESTIGATION OF EFFECT OF SINTERING TEMPERATURE

Stannic oxide was prepared via the controlled hydrolysis of an aqueous $SnCl_4$ solution by urea at 90° C. The gelatinous precipitate obtained was washed thoroughly with distilled water until the chloride concentration in the filtrate became negligible. After drying, heat treatment of the α-stannic acid in air at 800° C. for 2 hours ensured complete conversion to tin (IV) oxide. A fine homogeneous powder was obtained by grinding the oxide in a ball mill for 30 minutes.

Sensors were prepared by applying an aqueous paste of the $SnO_2$ across the contact pads of an alumina substrate (supplied by Rosemount Engineering) as described in previous publications [13, 14]. For sintering temperatures of 800° C. to 1000° C., the whole tin dioxide/substrate assembly was placed directly in the furnace in air. However, due to the inability of the substrate to withstand temperatures exceeding 1000° C., heat treatment (calcining) of the $SnO_2$ between 1100° C. and 1600° C. was performed on the free powder in air. The precalcined oxide was then applied to the substrate and fired at 1000° C. in the usual manner.

Full details of the procedure adopted for determining sensor resistance and blending mixtures of CO, $CH_4$ or $H_2$ in an oxygen-nitrogen supporting gas are given elsewhere [13, 14, 19].

Figure 1:
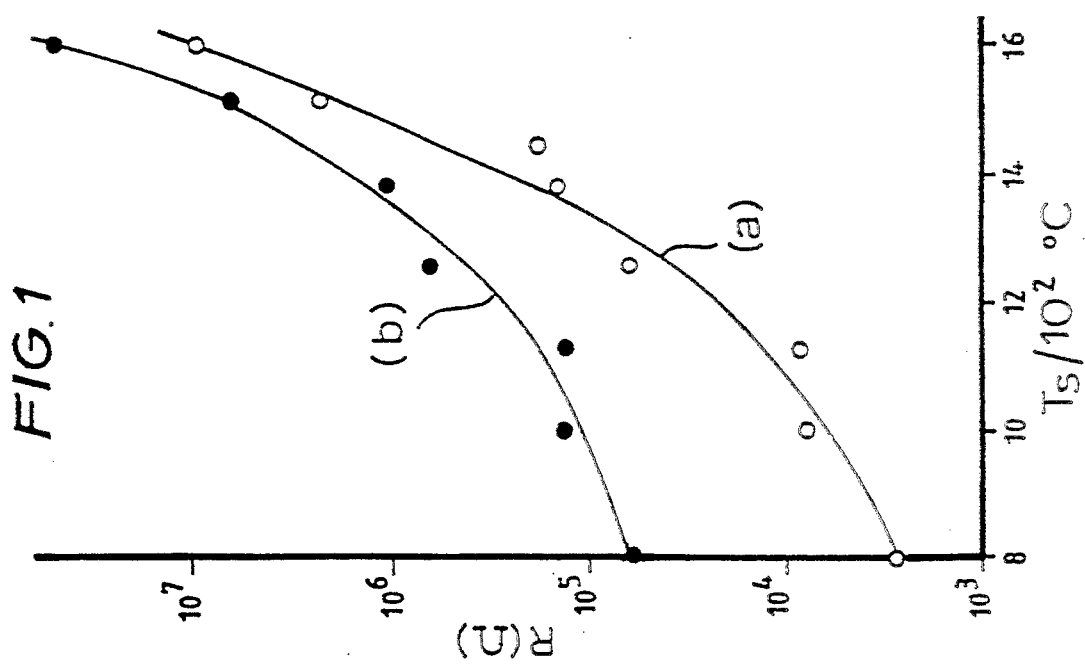
FIG. 1: Variation of sensor resistance as a function of $SnO_2$ sintering temperature at (a) $T_o$=400° C. and (b) $T_o$=280° C.

A study of the sensor resistance versus working temperature ($T_o$) relationship in clean dry air shows that increasing the $SnO_2$ sintering temperature leads to a substantial rise in resistance. FIG. 1 illustrates the change in sensor resistance observed at two different values of $T_o$ for $SnO_2$ samples sintered between 800° C. and 1600° C. The greatest increases in resistance are exhibited upon sintering the material at temperatures in excess of 1400° C. This result appears to conflict somewhat with the findings of Sasaki et al [12] who observed a fall in sensor resistance at sintering temperatures in excess of 1300° C. which they ascribe to the formation of 'necks' between separate oxide particles.

Figure 2:
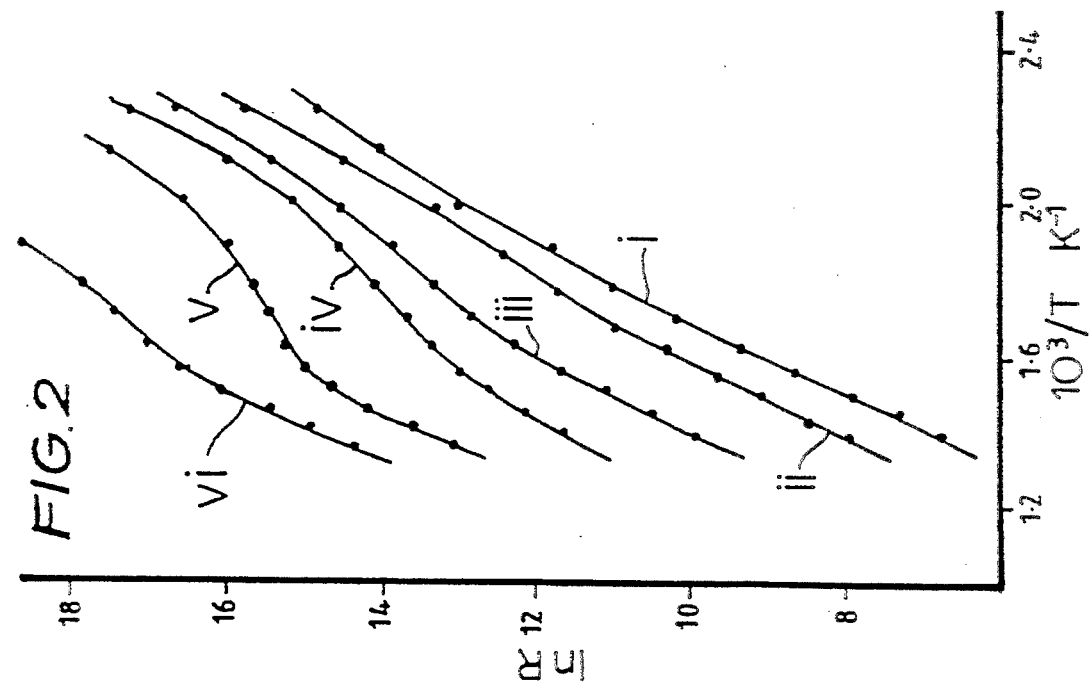
FIG. 2: Arrhenius-type plots of lnR versus $T^{-1}$ for a series of sensors fabricated from $SnO_2$ samples preheated at the following temperatures: (i) 800° C., (ii) 1125° C., (iii) 250° C., (iv) 1440° C., (v) 1500° C. and (vi) 1580° C.

Arrhenius type treatment of the data obtained for several sensors employing a range of sintering temperatures are shown in FIG. 2 [Sintering temperatures are:—(i) 800° C., (ii) 1125° C., (iii) 1250° C., (iv) 1440° C., (v) 1500° C. and (vi) 1580 ° C]. A curious characteristic of these plots is the gradual appearance of an inflection in the resistance-temperature curve between 230° C. and 350° C. as $T_S$ is increased. Such behaviour has been observed in previous studies on the electrical conductance of pressed porous pellets of $SnO_2$ sintered at 1000° C. [17] and attributed to a change in the absorbed oxygen species present on the sensor surface. However, the inflection manifests itself at a temperature which is significantly higher than the well established value of 160° C. determined for the $O_2^- \to 2O^-$ transformation [19].

The slopes of the lnR versus $T^{-1}$ plots for working temperature exceeding 350° C. vary only marginally with sintering temperature ($T_S$) as shown in Table 1.

TABLE 1

Effect of sintering temperature on the slopes of Arrhenius plots obtained in the 320° C. to 500° C. region for undoped $SnO_2$ sensors.

| Sintering Temperature/°C. | Arrhenius slope/eV |
|---|---|
| 800 | 0.95 |
| 1000 | 0.99 |
| 1125 | 0.90 |
| 1250 | 0.90 |
| 1375 | 0.85 |
| 1440 | 0.74 |
| 1500 | 0.91 |
| 1580 | 0.95 |

The high temperature activation energy determined for a $SnO_2$ sensor sintered at 1000° C. corresponds well with the findings of Moseley et al [17]. From their results these authors deduce that a surface state associated with adsorbed oxygen is located at 1.1 eV below the conduction band,.

Many authors have observed that the $SnO_2$ grain size increases with increasing values of $T_S$ and that a rise in sensor resistance also ensues [8, 12, 20]. Sasaki and his co-workers [12] have assigned this increase in resistance to the elimination of shallow donor levels as the sintering temperature is increased. However, it may also be possible than an enlargement in the crystallite size leads to a decrease in the number of intergrain boundaries thus restricting the flow of carriers through the sintered mass of material.

Figure 3A:
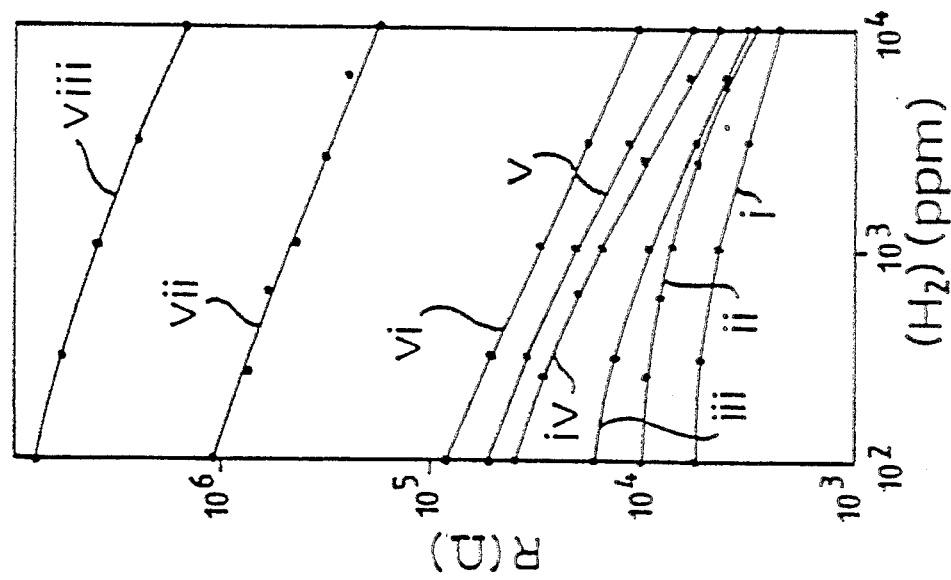
FIG. 3: Logarithmic plots of resistance versus reducing gas concentration at a working temperature of 400° C., for a series of sensors sintered at temperatures of (i) 800° C., (ii) 1000° C., (iii) 1125° C., (iv) 1250° C., (v) 1375° C., (vi) 1440° C., (vii) 1500° C. and (viii) 1580° C. The contaminant gases used in each case are (a) CO, (b) $CH_4$ and (c) $H_2$.
Figure 3B:
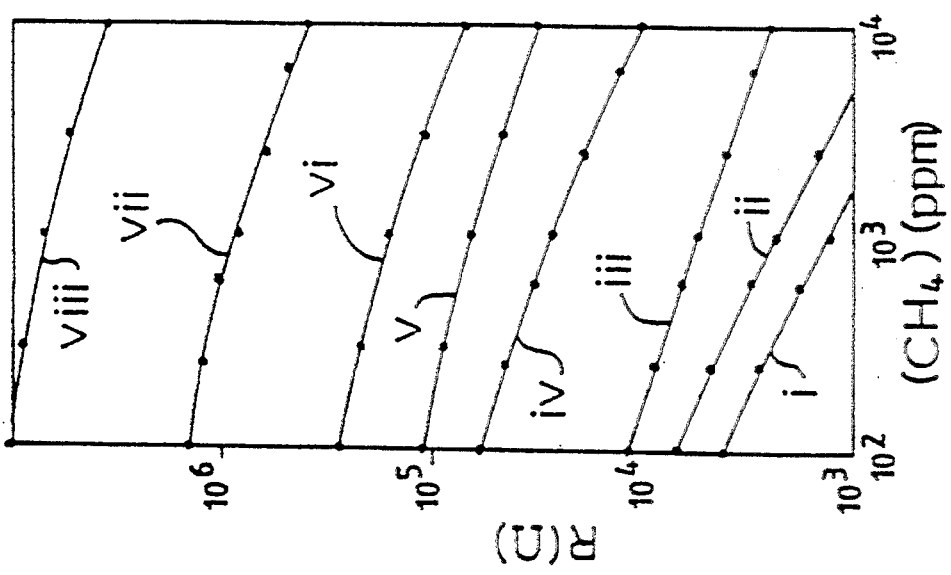
Figure 3C:
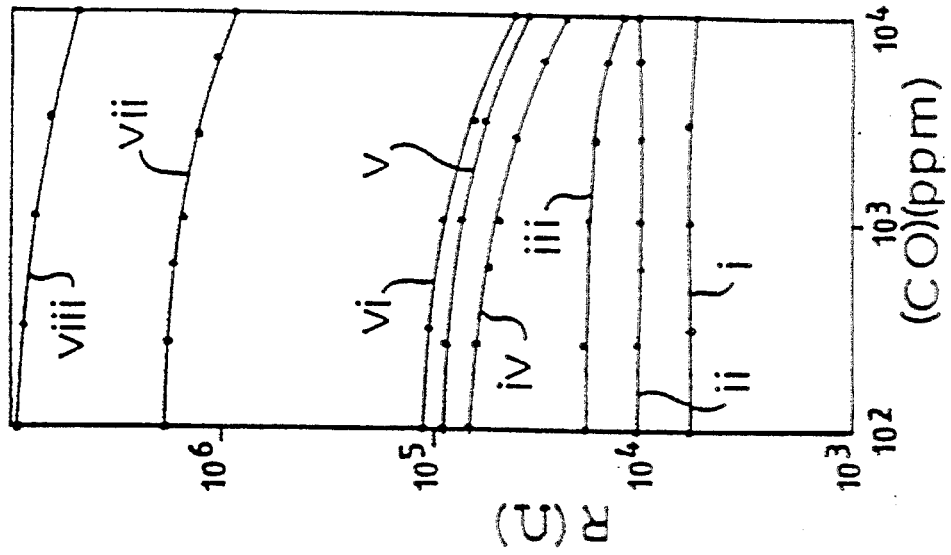

FIG. 3(a)-(c) illustrates the variation of sensor resistance at ≈400° C. as a function of contaminant gas concentration for a series of $SnO_2$ samples sintered in the range 800° C.<$T_S$>1600° C. [Sintering temperatures are:—(i) 800° C., (ii) 1000° C., (iii) 1125° C., (iv) 1250° C., (v) 1375° C., (vi) 1440° C., (vii) 1500° C. and (viii) 1580° C.]. The main characteristics of sensor response to each reducing gas tested will be discussed in turn.

(a) CO response

Sensors sintered at 800° C. or 1000° C. appear to possess little or no response to carbon monoxide at operating temperatures equal to or exceeding 400° C. However, increasing $T_S$ beyond 1100° C. appears to confer a degree of CO sensitivity which reaches a maximum at circa 1250° C. A sensor fabricated from a $SnO_2$ sample pretreated at this temperature exhibits a 66% resistance drop upon exposure to a 1% v/v CO/air mixture. Further increasing $T_S$ diminishes the CO signal to a certain extent, yet the response even at the highest sintering temperature employed remains significant.

(b) $CH_4$ response

The use of the lowest sintering temperatures yield sensors possessing high sensitivity to methane. An increase in $T_S$ leads to a gradual decline in the $CH_4$ signal, with the consequence that the $SnO_2$ sample sintered at the highest temperature generates the least sensitive element.

(c) $H_2$ response

The magnitude of resistance changes observed upon exposure to hydrogen inclusion for sensors employing $T_S \leq 51000°$ C. appear relatively insubstantial compared to the response exhibited in the presence of an equally concentration of methane. However, increasing the temperature of sintering initiates a substantial hydrogen sensitivity which reaches a maximum at around 1400° C. The use of higher values of $T_S$ leads to the desensitisation of the $H_2$ signal.

The trends described above are adequately represented by FIG. 4 where the ratio $R_o/R$ (where $R_o$=sensor resistance in clean air and R=sensor resistance in a 1% v/v contaminant/air mixture) is plotted as a function of sintering temperature. Therefore, if an undoped tin oxide sensor of this type is to be operated at a relatively high temperature ($T_o$=400° C.) then the greatest degree of selectivity to a certain gas, namely methane, is achieved by employing a sintering temperature in the range 800° C.-1000° C. However, should sensitivity to a range of reducing gases be the main requirement, the use of $T_S$ in the range 1250° C.-1400° C. would be most advantageous.

The logarithmic plots of sensor resistance versus contaminant gas concentration illustrated in FIG. 3(a)-(c) indicate that a power law relationship is obeyed by the majority of sensors. However, sensor response, especially to carbon monoxide, appears in several cases merely to asymptotically approach the power law relationship at high contaminant levels. Similar characteristics have been reported by others [21] during studies of the stead state gas response of TGS semiconductor gas sensors. The power law coefficient ($\beta$) varies considerably with sintering temperature as can be ascertained from the data presented in Table 2(a). Again the general trends in the magnitude of $\beta$ mirror those observed for the variation of CO, $CH_4$ and $H_2$ sensitivity with $T_S$ as discussed above.

TABLE 2

Variation of $\beta$, the power law slope as a function of sintering temperature for undoped $SnO_2$ sensors maintained at two different working temperatures upon exposure to inclusion of CO, $CH_4$ or $H_2$ in air.

| (a)$T_o$ = 400° C. Sintering Temperature/°C. | $\beta$(CO) | $\beta$(CH$_4$) | $\beta$H$_2$) |
|---|---|---|---|
| 800 | 0 | 0.49 | 0.30 |
| 1000 | 0 | 0.54 | 0.35 |
| 1125 | 0.10 | 0.37 | 0.45 |
| 1250 | 0.32 | 0.47 | 0.54 |
| 1375 | 0.25 | 0.34 | 0.54 |
| 1440 | 0.36 | 0.36 | 0.45 |
| 1500 | 0.22 | 0.33 | 0.39 |
| 1580 | 0.18 | 0.36 | 0.44 |
| (b)$T_o$ = 280° C. Sintering Temperature/°C. | $\beta$(CO) | $\beta$(CH$_4$) | $\beta$H$_2$) |
| 800 | 0.38 | 0.46 | 0.95 |
| 1000 | 0.40 | 0.35 | 0.86 |
| 1125 | 0.25 | 0.39 | 0.68 |
| 1250 | 0.19 | 0.43 | 0.47 |
| 1375 | 0.15 | 0.22 | 0.53 |
| 1440 | −0.10* | 0.12 | 0.34 |
| 1500 | −0.72* | 0.06 | 0.51* |
| 1580 | −0.14* | 0.04 | 0.22 |

*In cases where two types of behaviour are exhibited by the resistance versus gas concentration plots, the slope obtained in the $10^2$-$10^3$ ppm region is displayed.

Identical experiments to those described above were performed at a lower working temperature of 280° C. This temperature was established previously [18] as the optimum required for maximum sensitivity to carbon monoxide and hydrogen. The plots of sensor resistance versus contaminant gas concentration obtained for the series of sensors fabricated from $SnO_2$ samples preheated over a range of temperatures are shown in FIG. 5(a)-(c). Sensor properties at $T_o$=280° C. differ in several ways to those exhibited at a high working temperature.

(a) CO response

A significant decline in carbon monoxide sensitivity is observed upon increasing the temperature of sintering from 800° C. to 1375° C. Sensors fabricated from $SnO_2$ heat treated at temperatures equal to or exceeding 1440° C. display p-type behaviour upon exposure to CO inclusion of less than $10^3$ ppm. The most magnified resistance rises are observed when a sintering temperature of 1500° C. is employed. Increasing the CO concentration above $10^3$ ppm in this case causes diminution and eventual cessation of the resistance increments observed.

(b) $CH_4$ response

A decline in methane sensitivity with increasing temperature is displayed at the lower operating temperature, in accordance with the results attained at $T_o \approx 400$ C. However, at pretreatment temperatures of 1500° C. or above, $CH_4$ response becomes negligible.

(c) $H_2$ response

The use of the lowest sintering temperatures confers a substantial hydrogen sensitivity, which decreases as $T_S$ is raised. Curiously, a sensor fabricated from an $SnO_2$ sample sintered at 1500° C. exhibits conventional n-type behaviour upon exposure to hydrogen concentrations of less than $10^3$ ppm, yet as $H_2$ levels are increased further, sensor resistance rises significantly. This anomaly is not displayed by the sensor sintered at 1580° C.

Table 2(b) shows the effect of sintering temperature on B, the power law coefficient calculated from the plots illustrated in FIG. 5(a)-(c), at a sensor working temperature of 280° C. Again the variation of $\beta$ with sintering temperature is very substantial especially in the case of CO where a switch from a positive to a negative power law coefficient is observed at $T_S \approx 1440°$ C. It can be seen that the magnitude of the power law slope for $H_2$ gas is approximately a factor of 2 greater than for CO or $CH_4$ at sintering temperatures of less than 1125° C. This finding concurs with previously published results [21].

The gas sensing properties of polycrystalline $SnO_2$ sintered at 1500° C. were studied in view of its switch from n-type to p-type behaviour depending upon the conditions employed. The vast discrepancies in sensor response to reducing gases at the two operating temperatures utilised above ($\approx 400°$ C. and $\approx 280°$ C.) indicate that temperature is crucial in determining the behaviour of the sensor. The results of an exhaustive study of the effect of the variation of $T_o$ upon sensor response is represented in FIG. 6(a)–(c) where sensor resistance is plotted as a function of contaminant gas concentration using logarithmic axes [Working temperatures of (i) 450° C., (ii) 400° C., (iii) 360° C., (iv) 320° C., (v) 280° C., (vi) 230° C. and (vii) 175° C.].

If maintained at temperatures of 360° C. or above, the sensor experiences a drop in resistance upon exposure to CO, $CH_4$ or $H_2$ inclusions in air, as would be expected for this type of device. Decreasing $T_o$ below 360° C. produces several effects. Firstly, the resistance changes observed upon exposure to methane become negligible at working temperatures of 280° C. or less. However, secondly and more striking is the change in the mechanism of detection of CO exhibited by the sensor, where substantial increases in resistance are observed in the presence of CO/air mixtures. The magnitude of the p-type response reaches a maximum at $T_o \approx 230°$ C., where a 16 fold rise in sensor resistance is experienced in a 1% v/v CO atmosphere. Lowering the working temperature further leads to a severe reduction in the size of the p-type effect. A similar 'reverse sensitivity' is also exhibited upon exposure to hydrogen-containing environments at working temperatures of 280° C. or less. In this case the most enhanced increase in resistance is observed at the lowest value of $T_o$ used.

Figure 7:
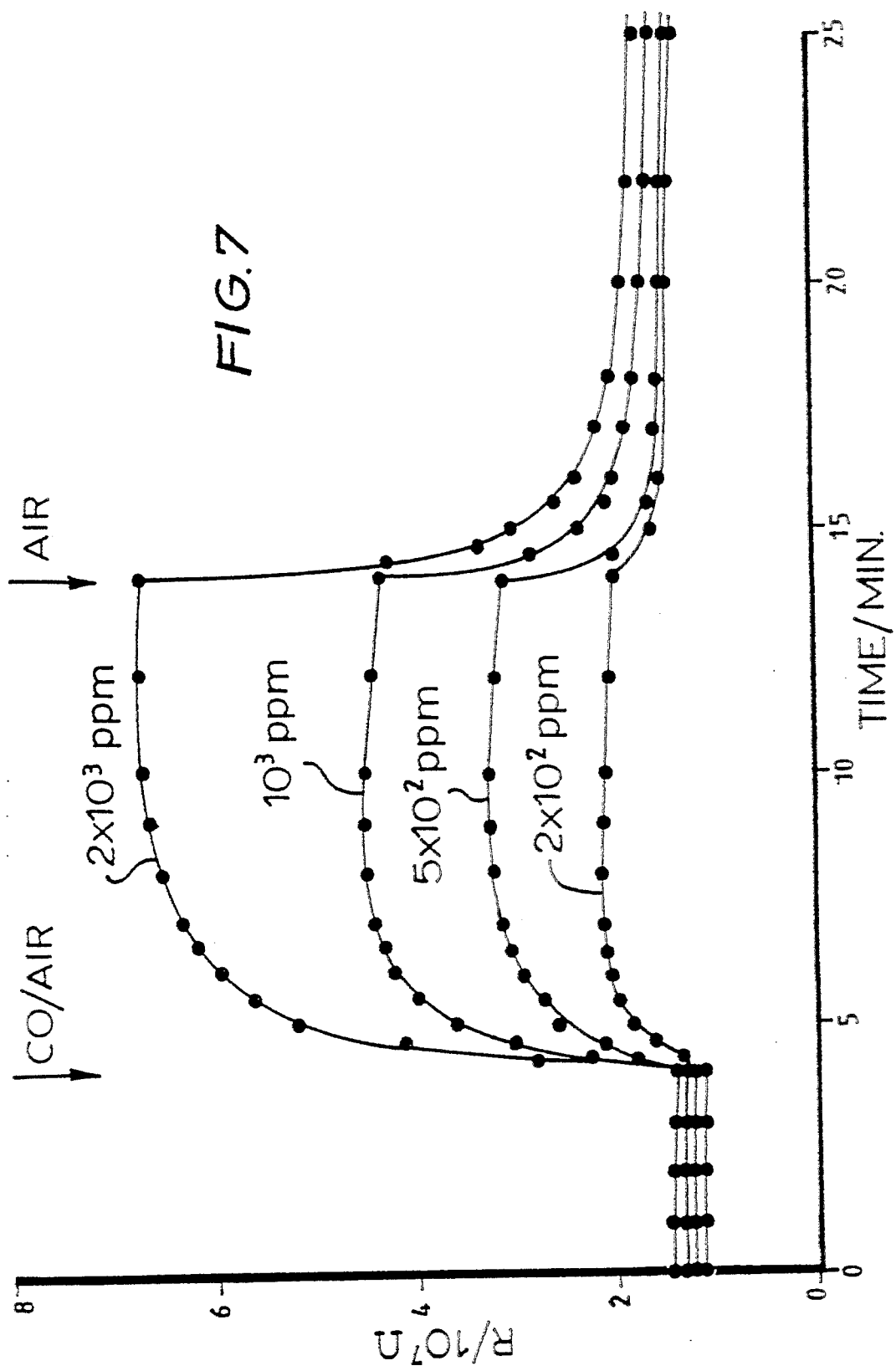
FIG. 7: Dynamic response of a sensor fabricated from $SnO_2$ preheated at 1500° C. to different CO concentrations in air. The operating temperature used is 280° C.

The dynamic response of the sensor maintained at $T_o \leq 280°$ C. appears substantially slower than the n-type signal observed at high operating temperatures. In the latter instance, the final resistance reading is reached 30 seconds or less after exposure to the reducing gas. However, at $T_o \approx 280°$ C. the resistance versus time profiles plotted in FIG. 7 shows that the final signal is only attained circa 5 minutes after introduction of the CO/air mixture. Recovery of the original resistance in air appears even slower, taking up to 30 minutes when the sensor has previously been dosed with carbon monoxide concentrations of 0.5% v/v or greater.

The reproducibility of the phenomenon for several sensors prepared from different batches of $SnO_2$ sintered at 1500° C. was investigated. These experiments revealed that this p-type behaviour was displayed in all cases, but the magnitude of the observed resistance increases for a fixed CO or $H_2$ concentration varied significantly between tin oxide batches.

In a separate investigation, the effect of different oxygen partial pressures on sensor response at operating temperatures of 280° C. or less were studied. FIG. 8(a) illustrates the change in the ratio $R/R_o$ (defined previously) for a 1% v/v CO inclusion as the oxygen partial pressure ($P_{o2}$) is decreased from 1 to $10^{-4}$ atm. A steady decline in the p-type response is observed as $P_{o2}$ is lowered in supporting gas only i.e. a conventional n-type detection mechanism. The results of a similar study of the oxygen dependence of $H_2$ response at $T_o = 175°$ C. are also included in FIG. 8(a). Here the resistance increment observed upon dosing with 1% v/v $H_2$ inclusions remains constant at $P_{o2}$ is decreased from 1 to $10^{-2}$ atm. However, further reduction of $P_{o2}$ results in the curtailment of the signal until changes become insignificant when the oxygen partial pressure is $10^{-4}$ atm.

FIG. 8(b) shows the sensor response characteristics at $T_o = 280°$ C. when $P_{o2}$ in the base gas is fixed at $10^{-4}$ atm. and the reducing gas concentration is varied. As can be seen from the resistance versus [CO] or [$H_2$] plots obtained, sensor behaviour has reverted to conventional n-type, while sensitivity to $CH_4$ remains virtually negligible. The resistance response of the sensor to oxygen in the absence of reducing gas revealed that a power law relation exists. A value of 0.29 was determined for B, the power law slope from a logarithmic plot of sensor resistance versus $P_{o2}$.

How exactly the observed change in the $SnO_2$ gas detection mechanism arises is unclear. Other researchers [22, 23] have observed similar phenomena during their investigation of $ThO_2$—or $ZrO_2$ - doped tin oxide sensors sintered at 600° C. or 800° C. respectively. An increase in sensor resistance occurs as the $ThO_2$—added $SnO_2$ sample is exposed to appropriate concentrations of hydrogen at temperatures of 220° C. or lower [22], while the $ZrO_2$—doped material acts similarly in the presence of ammonia [23]. Kanefusa et al [22] tentatively suggests that this negative sensitivity is caused by a change in adsorption rates or physical nature of the adsorbates on the sensor surface under these conditions. It may be possible that the change in response is due to a high temperature calcining induced change in the nature of the non-stoichiometry of the tin oxide resulting in differing charge carriers being responsible for high and low temperature conductivity. It may be possible that preheating undoped $SnO_2$ at a temperature of 1500° C. modifies the sensor surface to a considerable extent thus allowing such changes to occur.

Previously reported studies of the effects of thermal pretreatment on the properties of $SnO_2$ [24, 25] have concentrated for the most part on the catalytic activity of tin oxide annealed in the 200° C. to 800° C. region in mediating a range of oxidation reactions. However, a more fundamental investigation by Goodman and Gregg [8] shows that significant charges occur to $SnO_2$ upon high temperature sintering. These authors report that the specific surface area of stannic oxide is markedly reduced upon increasing the calcination temperature from 250° C. to 1400° C., but this is only accompanied by a minimal change range in pore volume. However, at a temperature of circa 1550° C. the pore volume suddenly falls to zero, an occurrence that is liable to have a critical influence on the sensing properties of a device fabricated from such a material.

Figure 9C:
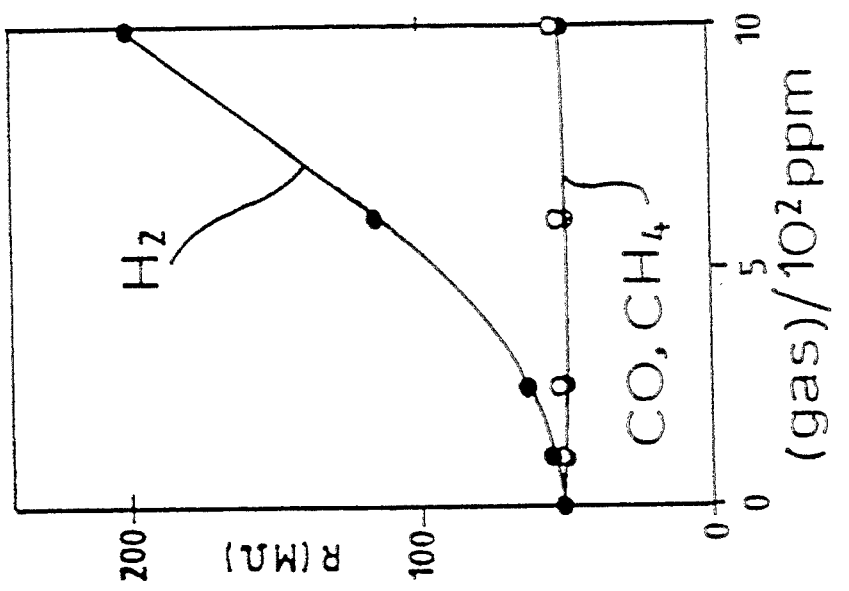
FIG. 9: Resistance versus contaminant gas concentration plots for a sensor fabricated from $SnO_2$ pre-sintered at 1500° C. in air and maintained at three different operating temperatures; (a) 400° C., (b) 280° C. and (c) 175° C.
Figure 9B:
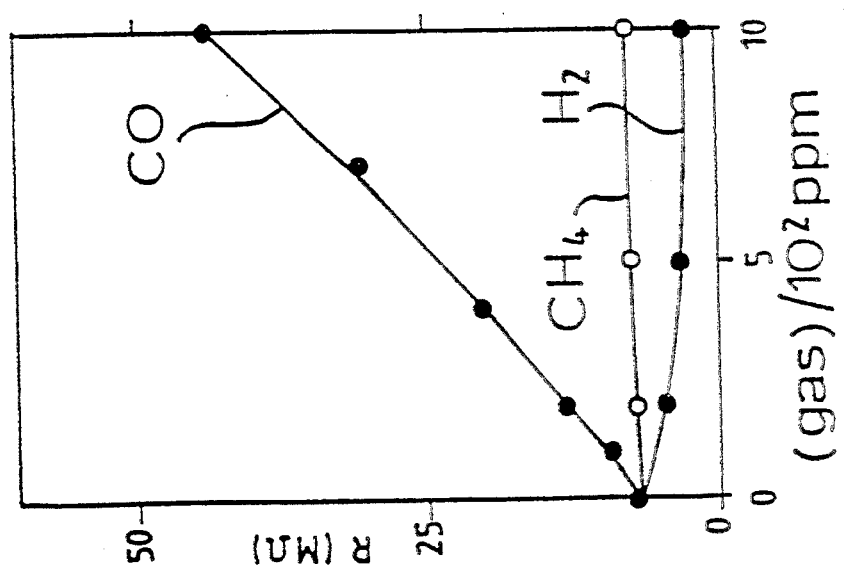
Figure 9A:
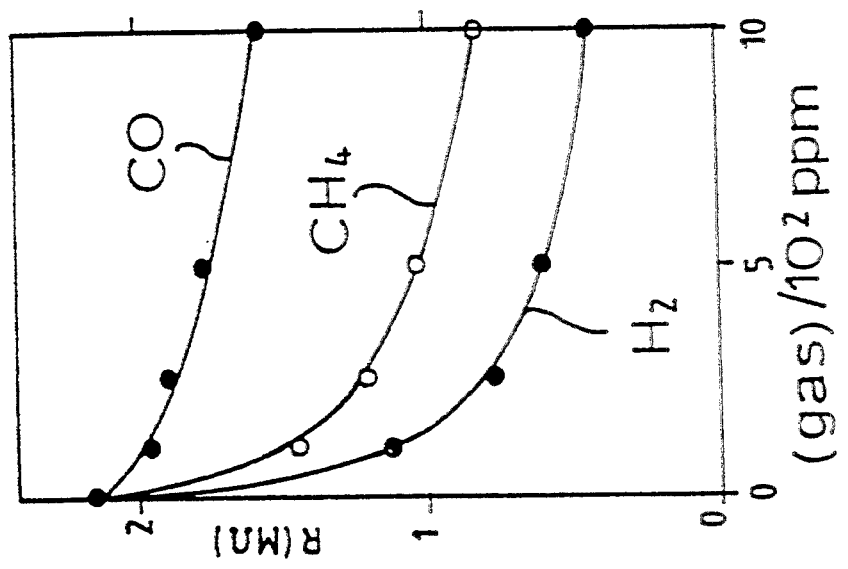

A more detailed study of the properties of this sensor entailed the determination of response to other reducing gases such as methane or hydrogen over a range of working temperatures. The results obtained are summarised in FIG. 9 where the variation of sensor resistance as a function of CO, $CH_4$ or $H_2$ concentration is monitored at operating temperatures of 400° C., 290° C. and 175° C. respectively. As would be expected for this type of n-type semiconducting material, at working temperatures of 360° C. or above the sensor experiences a drop in resistance upon exposure to each contaminant gas tested. However, should the device be operated at temperatures below 360° C. several changes in sensor behaviour are manifested. Firstly, the resistance changes observed in the presence of methane inclusions become negligible at working temperatures of 280° C. or less. However, secondly and more striking is the change in the mechanism of CO exhibited by the sensor where substantial increases in resistance are observed in the presence of carbon monoxide/air mixture.

The magnitude of the p-type response reaches a maximum at 230° C. where a 16 fold rise in resistance is experienced in a 1% v/v CO atmosphere. Further reduction of the operating temperature leads to a similar reverse sensitivity to $H_2$ as shown in FIG. 2(c), but a severe decrease in the p-type effect observed for carbon monoxide.

The inventors' studies have revealed that sensor characteristics vary considerably with the $SnO_2$ pre-treatment temperature. The use of $T_S=800°$ C. or $1000°$ C. confers greatest methane sensitivity at high sensor working temperatures and maximum CO or $H_2$ response for $T_2=280°$ C. If a sensor is to be maintained at circa $400°$ C. then the greatest hydrogen and carbon monoxide sensitivity is obtained by utilising sintering temperatures in the $1250°$ C.–$1400°$ C. range.

A sensor prepared from a tin oxide sample fired at $1500°$ C. displayed some remarkable properties. If this type of device is operated at $400°$ C. then the resistance of the sensor decreases in the presence of CO, $CH_4$ or $H_2$. However, the use of lower working temperatures leads to negative sensitivity to CO and $H_2$, i.e. sensor resistance increases significantly upon exposure to the reducing gas. Such anomalous behaviour may have important selectivity implications. A sensor maintained at $280°$ C. displays p-type response to CO, conventional n-type detection of $H_2$ and negligible sensitivity to $CH_4$. Therefore, a single sensor capable of discerning between different reducing gases if operated at several pre-set temperatures can be generated merely by utilising a high temperature sintering step prior to fabrication.

The p-type carbon monoxide or hydrogen response occurs despite apparent n-type semiconductivity revealed by resistance-temperature and resistance-oxygen partial pressure relationships. It is also known that the phenomenon is only exhibited in the presence of oxygen containing environments when $P_o$ exceeds $10^{-3}$ atm.

INVESTIGATION OF EFFECT OF SENSOR BASE RESISTANCE & DOPANTS

Tin oxide sensors were made for experimental purposes from an aqueous slurry containing $SnO_2$, $Sb_2O_3$ (1–3% w/w). No metal catalyst was added or necessary. The $SnO_2$ was made by hydrolysis of $SnCl_4$ (BDH 'Analar' grade) and ground with an appropriate amount of $Sb_2O_3$ (Johnson Matthey Chemicals 'Specpure' grade) typically to <15 μm. A bead of this paste was then applied across platinum contact pads deposited on an alumina substrate (Rosemount) left to dry in air and then sintered at $1000°$ C. for 2 hours (using a furnace heating rate of $400°$ C./hour).

Figure 10:
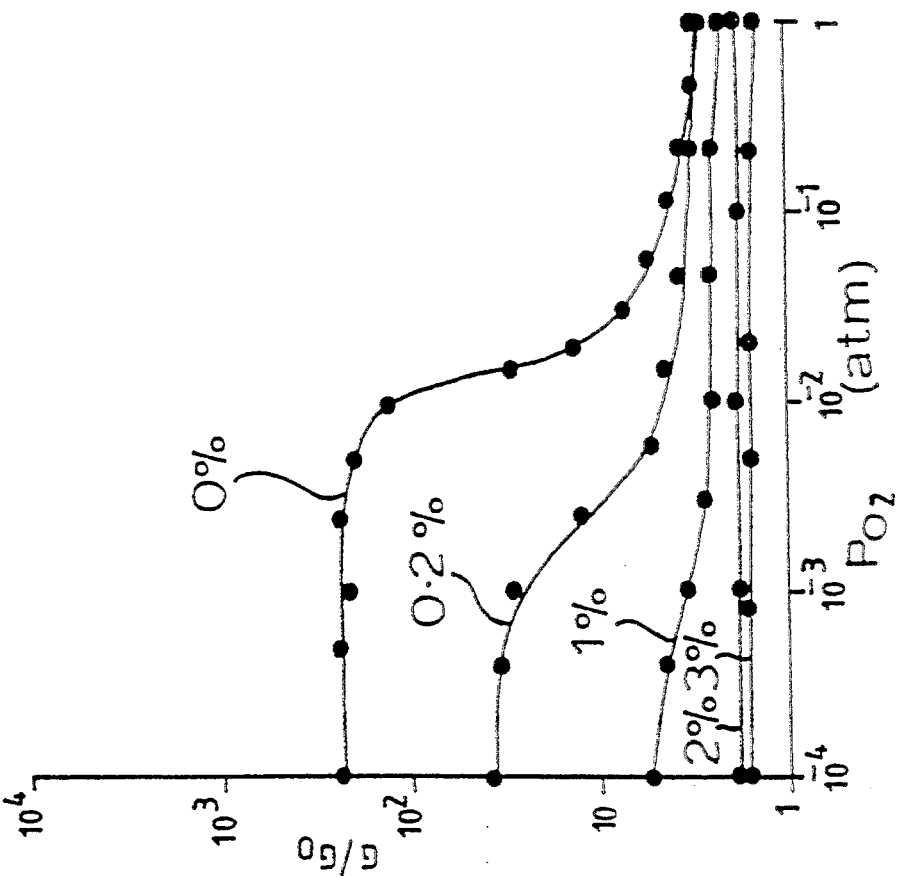
FIG. 10 is a graph indicating the response of a series of $Sb_2O_3$ doped tin oxide sensors (measured as $G/G_o$, where G=conductance in a contaminant—$O_2$—$N_2$ mixture and $G_2$=conductance in supporting gas only) to a 1% v/v carbon monoxide inclusion plotted as a function of oxygen partial pressure.
Figure 11:
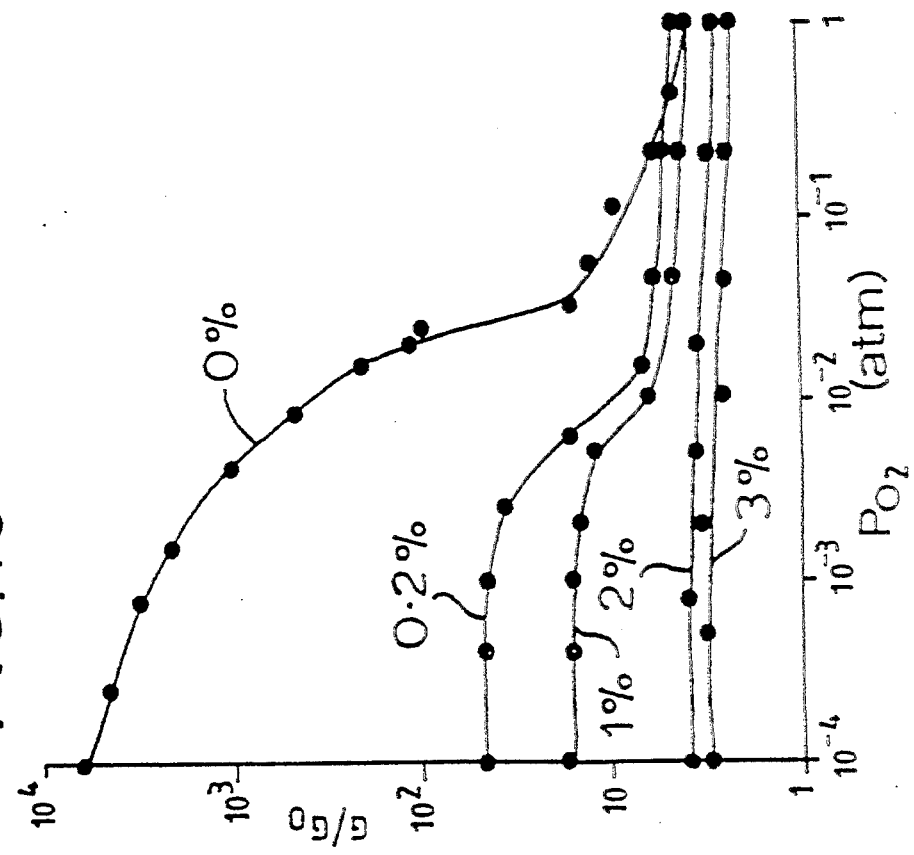
FIG. 11 as FIG. 10 except that a 1% v/v methane inclusion was used.
Figure 12:
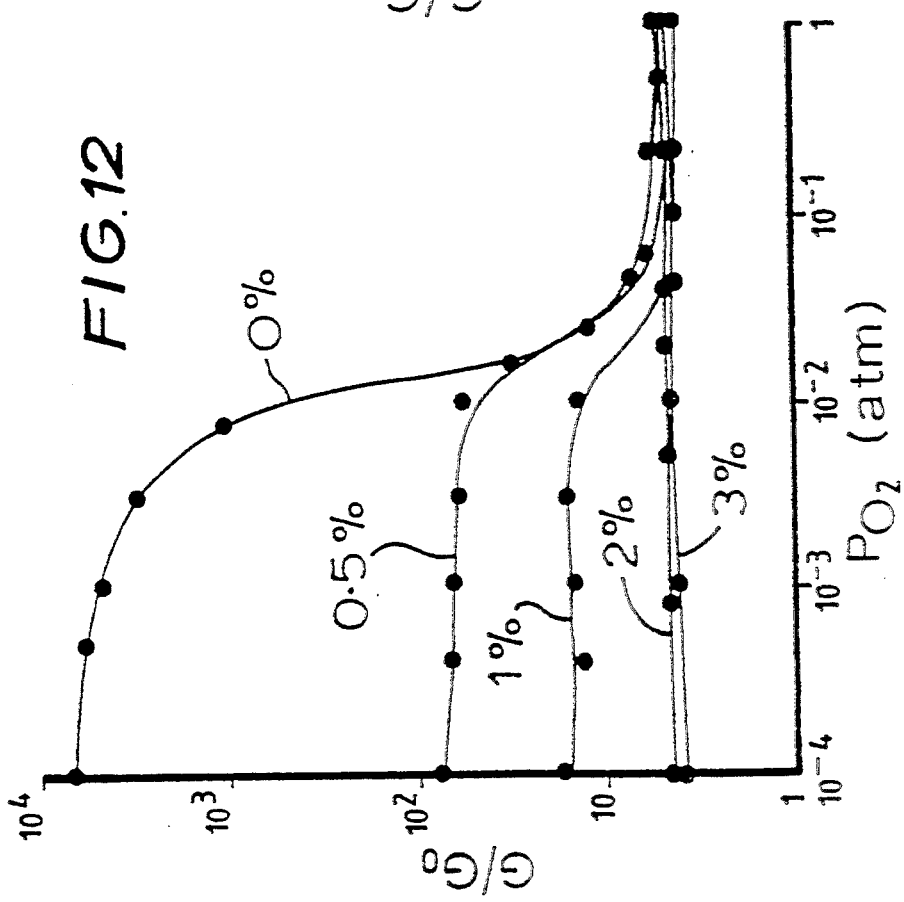
FIG. 12 as FIG. 10 except that a 1% v/v hydrogen inclusion was used.

Illustrated in FIG. 10 is the CO response of several Sb doped sensors plotted as a function of oxygen partial pressure. The response in this case is represented by the ratio $G/G_o$ where $G_o$=sensor conductance in the $O_2/N_2$ base mixture and G=conductance observed in the presence of a 1% v/v contaminant gas inclusion. The data presented show that even a very small quantity of added $Sb_2O_3$ (0.2% w/w) reduces the observed response at the lowest oxygen concentration tested by over 2 orders of magnitude. Further increase of the sensor $Sb_2O_3$ content leads to the complete elimination of any increase in CO response as $P_{O2}$ is decreased in the range $1$–$10^{-4}$ atm. This effect is also observed for other reducing gases such as $CH_4$ (FIG. 11) and hydrogen (FIG. 12). A direct comparison of sensor response in two different oxygen containing environments is shown in Table 3.

TABLE 3

A comparison of the response of a series of $Sb_2O_3$ doped tin dioxide sensors observed in air and under conditions of greatly reduced oxygen partial pressure.

| Environment 1: | Air ($P_{O2}$ - 0.21 atm.) | | |
|---|---|---|---|
| % $Sb_2O_3$ (w/w) | *$G/G_O$ (CO) | $G/G_O$ ($CH_4$) | $G/G_O$ ($H_2$) |
| 0 | 4.80 | 3.57 | 4.60 |
| 0.2 | 4.64 | 3.40 | 14.0 |
| 0.5 | 3.21 | 2.21 | 5.44 |
| 1 | 4.10 | 2.48 | 3.99 |
| 2 | 2.76 | 1.53 | 4.62 |
| 3 | 2.33 | 1.72 | 4.20 |
| Environment 2: | $P_{O2}$ - $10^{-4}$ atm., balance $N_2$ | | |
| % $Sb_2O_3$ (w/w) | *$G/G_O$ (CO) | $G/G_O$ ($CH_4$) | $G/G_O$ ($H_2$) |
| 0 | 6400 | 230 | 6800 |
| 0.2 | 45 | 35 | 88 |
| 0.5 | 77 | 15 | 76 |
| 1 | 17 | 5.3 | 17 |
| 2 | 3.72 | 1.67 | 3.94 |
| 3 | 2.93 | 1.74 | 4.64 |

*Response in this type of study is represented by the ratio of sensor conductance in the presence of a 1% v/v contaminant gas inclusion to the conductance in supporting gas only.

The data listed for each reducing gas imply that a 2% w/w inclusion of $Sb_2O_3$ is sufficient to suppress any enhanced sensitivity at $P_{O2}=10^{-4}$ atm. while maintaining a reasonably substantial signal in air, e.g. a value of $G/G_O=4$ observed in the presence of a 1% v/v $H_2$ inclusion corresponds to a 75% drop in resistance.

The reasons for the action of $Sb_2O_3$ in suppressing oxygen dependence of sensor response remain unclear at present. It may be that the large number of electrons promoted from shallow Sb (III) donor levels eventually saturate the $SnO_2$ conduction band and conceal to a large extent any substantial increases in conductivity.

Some support for this suggestion can be obtained by comparing final resistance values for $SnO_2$ and Sb-doped sensors upon exposure to 1% v/v reducing gas at $P_{O2}=10^{-4}$ atm. (Table 5).

TABLE 5

| [$Sb_2O_3$] w/w | $R_{CO}$/kΩ | $R_{CH4}$/kΩ | $R_{H2}$/kΩ |
|---|---|---|---|
| 0 | 1.5 | 2.4 | 1.0 |
| 0.2 | 0.4 | 1.2 | 0.5 |
| 0.5 | 0.6 | 0.6 | 0.2 |
| 1 | 0.9 | 3.0 | 1.0 |
| 3 | 0.6 | 1.6 | 0.4 |

The variation between the resistance values listed above for each sensor appear small compared with the differences in original base resistance. It seems therefore that a point is reached beyond which sensor resistance cannot decrease any further, i.e. a minimum where the conduction band of the semiconductor is saturated.

The inventors attempted to test whether the low base resistance of the antimony doped sensors was the cause of their low oxygen cross-sensitivity. A series of additives were used on test sensors having the same geometry and the effect of these additives are summarised in Table 6 and 7 below.

Two different methods and media were used for applying the $SnO_2$ to form sensors. In the first method a tin oxide sample (prepared previously via the hydrolysis of $SnCl_4$ [BDH 'Analar' grade]) was ground in an aqueous paste along with the appropriate quantity of $Sb_2O_3$ typically to <15 μm. The $Sb_2O_3$ used for these experiments was obtained from Johnson Matthey Chemicals 'Specpure' grade. The paste was then applied across the electrode array of a gas sensor substrate, allowed to dry and then sintered in air at 1000° C. for 2 hours with additional two hour heating and cooling ramps.

When a tin oxide from Keeling & Walker ('Superlite' grade) was used in the above method it was found that cracking of the tin oxide resulted in a deficient sensor being formed. (The Keeling & Walker tin oxide contains significant amounts of antimony oxide and other trace materials). This defect could be avoided by forming the sensor in a non-aqueous medium. In this case the $SnO_2$—$Sb_2O_3$ mixture was ground in an inorganic media consisting of alpha-terpineol containing an ethyl cellulose (1% w/w) stabiliser. The mixture was ground to typically <15 μm. The paste was then applied to the substrate surface and dried for 1 hour at a temperature of 80° C. The sensor was then sintered using the conditions described above at 1000° C.

An advantage of forming the sensor from a slurry in the terpineol base is that by grinding to <15 μm a paste results which can be screen printed and this is useful in preparation of large numbers of sensors.

TABLE 6

| Additive | Medium of application to substrate | Power | Base resistance (Air) | Resistance when $P_{o2} = 10^{-4}$ atm |
|---|---|---|---|---|
| (1)$SnO_2$ (none) | Alpha-terpineol base | 3.27 W | 0.44 kohm | 0.23 kohm |
| (2)$SnO_2$ (none) | Aqueous paste | 3.04 W | 0.34 kohm | 0.12 kohm |
| (3)$MoO_3$ | Aqueous paste | 3.29 W | 2.90 kohm | 1.75 kohm |
| (4)$WO_3$ | Aqueous paste | 3.24 W | 4.40 kohm | 1.85 kohm |
| (5)$Nb_2O_5$ | Alpha-terpineol paste | 3.23 W | 78 kohm | 31 kohm |
| (6)$Sb_2O_3$ | Aqueous paste | 3.47 W | 9.1 ohm | 8.0 ohm |
| (7)$P_2O_5$ | Aqueous paste | 3.44 W | 0.74 kohm | 0.28 kohm |
| (8)$In_2O_3$ | Aqueous paste | 3.12 W | 2200 kohm | 510 kohm |
| (9)$Ta_2O_5$ | Alpha-terpineol paste | 3.23 W | 83 ohm | 40 ohm |
| (10)$B_2O_3$ | Aqueous paste | 3.32 W | 1.0 kohm | 0.44 kohm |
| (11)$RuO_2$ | Alpha-terpineol paste | 3.27 W | 1.45 kohm | 0.68 kohm |

TABLE 7

| Additive | Test gas | Sensitivity ($R_o/R_{gas}$) in Air | Sensitivity ($R_o/R_{gas}$) when $P_{o2} = 10^{-4}$ atm |
|---|---|---|---|
| (1)$SnO_2$ (none) | CO | 4.22 | 8.13 |
|  | $CH_4$ | 2.75 | 7.72 |
|  | $H_2$ | 8.52 | 28.0 |
| (2)$SnO_2$ | CO | 4.73 | 9.58 |
|  | $CH_4$ | 3.33 | 5.30 |
|  | $H_2$ | 7.81 | 14.1 |
| (3)$MoO_3$ | CO | 2.07 | 27.1 |
|  | $CH_4$ | 2.20 | 16.7 |
|  | $H_2$ | 4.25 | 174 |
| (4)$WO_3$ | CO | 2.21 | 50 |
|  | $CH_4$ | 1.69 | 12.5 |
|  | $H_2$ | 4.19 | 108 |
| (5)$Nb_2O_5$ | CO | 10.6 | 196 |
|  | $CH_4$ | 4.16 | 41 |
|  | $H_2$ | 17.4 | 375 |
| (6)$Sb_2O_3$ | CO | 1.46 | 1.41 |
|  | $CH_4$ | 1.22 | 1.15 |
|  | $H_2$ | 1.39 | 1.38 |
| (7)$P_2O_5$ | CO | 2.45 | 14.0 |
|  | $CH_4$ | 2.39 | 7.58 |

TABLE 7-continued

| Additive | Test gas | Sensitivity ($R_o/R_{gas}$) in Air | Sensitivity ($R_o/R_{gas}$) when $P_{o2} = 10^{-4}$ atm |
|---|---|---|---|
|  | $H_2$ | 13.5 | 15.7 |
| (8)$In_2O_3$ | CO | 8.15 | 1800 |
|  | $CH_4$ | 3.11 | 13.9 |
|  | $H_2$ | 68.6 | 12500 |
| (9)$Ta_2O_5$ | CO | 2.14 | 4.15 |
|  | $CH_4$ | 1.69 | 2.88 |
|  | $H_2$ | 3.79 | 5.67 |
| (10)$B_2O_3$ | CO | 6.47 | 33 |
|  | $CH_4$ | 5.20 | 18.8 |
|  | $H_2$ | 20.5 | 46.3 |
| (11)$RuO_2$ | CO | 4.05 | 12.9 |
|  | $CH_4$ | 2.31 | 5.0 |
|  | $H_2$ | 6.59 | 23.2 | to a large decrease in base resistance, comparable to that induced by antimony. However it is clear from Table 7 that despite this the ratio of sensitivity in air to sensitivity at $P_{O2}=10^{-4}$ remains close to that for un-doped tin oxide.

Figure 13:
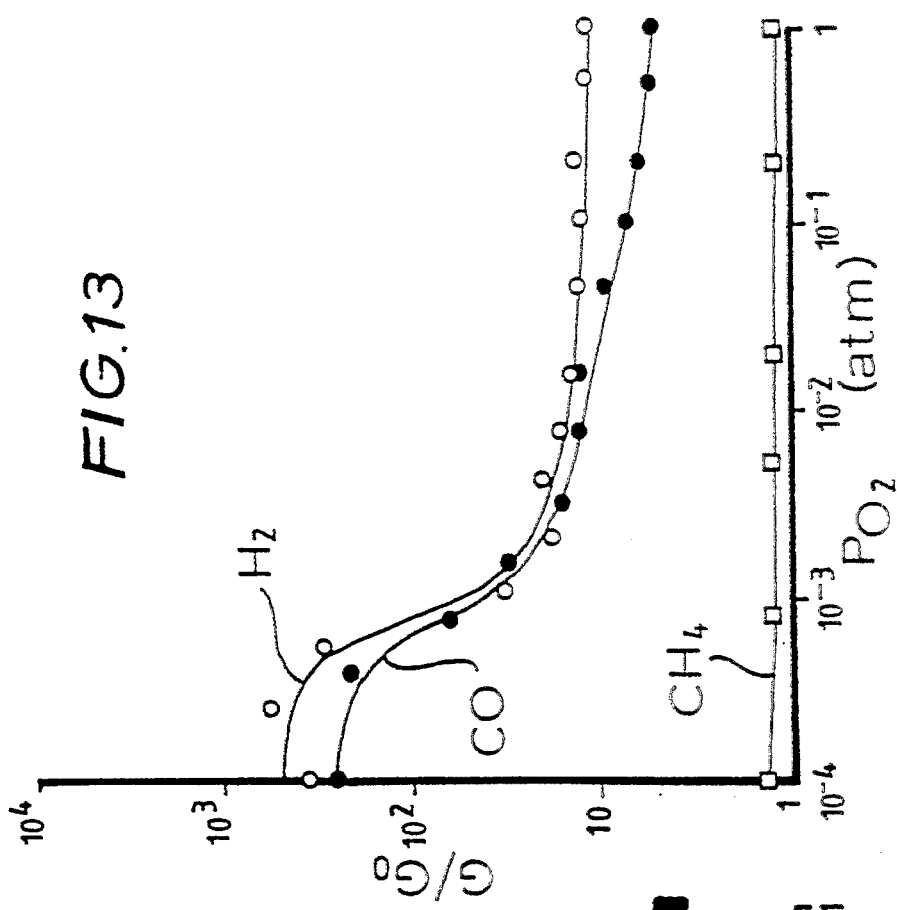
FIG. 13 Response ($G/G_0$) of a CO selective sensor doped with 2% w/w $Sb_2O_3$ plotted as a function of oxygen partial pressure. A contaminant gas concentration of 1% v/v was used in each case while the sensor was maintained at an operating temperature of 280° C.

In a separate experiment, to ascertain whether a CO sensor could be made having reduced oxygen cross-sensitivity, the behaviour of a sensor composed of $SnO_2$ (83%), $Bi_2O_3$ (15%) and $Sb_2O_3$ (2% w/w) in different oxygen containing environments was studied. Thins sensor was found to be CO and $H_2$ selective having a negligible response to $CH_4$. FIG. 13 illustrates the variation of sensor response to 1% v/v CO, $CH_4$ and $H_2$ inclusions as a function of oxygen partial pressure. In contrast to the $SnO_2$—$Sb_2O_3$ (2% w/w) system, this sensor exhibits significant increases in CO and $H_2$ response when PO2 is reduced below $10^{-3}$ atm. However, one advantage is that selectivity to these gases is retained[over a wide oxygen concentration range and $CH_4$ response remains negligible. The different behaviour in the presence or absence of $Bi_2O_3$ may perhaps be associated with the dissimilarity in the resistivities of both systems. $SnO_2$ reacts with $Bi_2O_3$ at temperatures in excess of 600° C. to form $Bi_2Sn_2O_7$, and this is accompanied by the consumption of a large number of conduction band electrons with the consequence that a large increase in resistance is observed. Though relatively high conductivity is restored upon the addition of $Sb_2O_3$ by promotion of electrons from Sb (III) donor levels, the occupancy of the conduction band is not sufficiently great to enable concealment of any large changes in sensor conductance.

This aspect of the invention does not include systems in which $Bi_2O_3$ or ,other materials are present which react with antimony to prevent its effect of suppressing oxygen cross-sensitivity.

Combined Unitray Sensor

From the above it will appear clear that the high temperature pre-calcined sensor exhibits a useful variance in behaviour with temperature such that it can be used at varying temperatures (either by varying the temperature of one sensor or using several sensors held at different temperatures) so as to enable determination of several gases. Indeed if several sensors are used they may advantageously be formed on a single substrate having separate heaters for each sensor.

The high temperature pre-calcined sensor shows oxygen cross-sensitivity at low oxygen concentrations ($<10^{-3}$ atm.) and so if an antimony doped sensor is also applied to the same substrate a comparison between the signal for a given as from the pre-calcined sensors and the antimony doped sensor will enable one to deduce the oxygen partial pressure.

Indeed it would also be possible to apply a linear-response hydrogen electrode to the same substrate.

Conventional circuit design principles will apply to determining the most appropriate lay-out of the sensors on the substrate but care must be taken to ensure that at the sintering stage elements such as bismuth and antimony do not migrate.

REFERENCES

1. J Watson 'The tin oxide gas sensor and its applications', Sensors and Actuators, 5, (1984), 29.
2. K. Ihokura 'Tin oxide gas sensor for de-oxidising gas', New Materials and New Processes, 1, (1981), 43.
3. H. Windischmann and P. Mark, 'A model for the operation of a thin film $SnO_x$ conductance-modulation carbon monoxide sensor', J. Electrochem, Soc. 126 (4), (1979), 627.
4. G. Heiland, 'Homogeneous semiconducting gas sensors', Sensors and Actuators, 2 (1982), 343.
5. N. Taguchi, Brit. Patents nos. 1 282 993, 1 288 009, 1 280 809, (1970).
b 6. Nitta and M. Hasadome, 'CO gas detection by $ThO_2$-doped $SnO_2$', J. Electron Mater., 8 (5), (1979), 571.
7. N. Yamazoe, Y. Kurokawa and T. Seiyama, 'Hydrogen sensitive gas sensor using silver added tin(IV) oxide', J. Chem, Soc., Japan, Chem.Lett., (1982), 1899.
8J. F. Goodman and S. J. Gregg, 'The Production of active solids by thermal decomposition. Part XI. 'The heat treatment of precipitated stannic oxide'. J. Chem. Soc., (1960), 1162.
9. S Yasunaga, S. Sunahara and K. Ihokura, 'Effects of tetraethyl orthosilicate binder on the characteristics of an $SnO_2$ ceramic-type semiconductor gas sensor', Sensors and Actuators, 9, (1986), 133.
10. K. Ihokura, K. Tanaka and N. Murakami, 'Use of tine dioxide sensor to control a domestic gas heater', Sensors and Actuators, 4, (1983), 607.
11. E. Borand, 'Influence of annealing temperature of non doped sintered tin oxide sensors on their sensitivity and response time to carbon monoxide'. Sensors and Actuators, 4, (1983), 613.
12. N. Murakami, K. Tanaka, K. Sasaki and K. Ihokura, 'The influence of sintering temperature on the characteristics of $SnO_2$ combustion monitor sensors', Anal. Chem. Symp, Ser., 17, (Chem. Sens), (1983), 165.
13. G. S. V. Coles, K. J. Gallagher and J. Watson, 'Fabrication and preliminary tests on tin (IV) oxide-based gas sensors', Sensors and Actuators, 7, 2, (1985), 89.
14. G. S. V. Coles, G. Williams and B. Smith, 'Selectivity studies on Tin Oxide-based semiconductor gas sensors', Sensors and Actuators, 3, 1, (1991) 7.
15. L. N. Yannopoulos, 'Antimony-doped stannic oxide-based thick-film gas sensors', Sensors and Actuators, 12, (1987), 77.
16. H. Torvela, P. Romppainen and S. Leppavuori, 'Detection of CO levels in combustion gases by thick film $SnO_2$ sensor', Sensors and Actuators, 14, (1988), 19.
17. J. F. McAleer, P. T.Moseley, J. D. W. Norris and D. E. Williams, 'Tin dioxide gas sensors. Part I—Aspects of the surface chemistry revealed by electrical conductance variations'. J. Chem. Soc., Faraday Trans. 1, 83, (1987), 1323.
18. G. S. V. Coles, G. Williams and B. Smith. 'The effect of oxygen partial pressure in the supporting gas on the response of tin(IV) oxide based sensors', accepted for publication in J. Phys. D.
19. S-C Chang, 'Oxygen chemisorption on tin oxide: correlation between electrical conductivity and EPR measurements', J. Vac. Sci. Technol., 17 (1), (1980), 366.
20. S. Novel, C. Pijolat, R. Lalauze, M. Loesch and C. Combes, 'Influence of grain size and working temperature on the performance of a sensor produced from polycrystalline tine oxide', article presented at the Sensors and their Applications IV Conference, Canterbury, 1989.
21. P. K. Clifford and D. T. Tuma, 'Characteristics of semiconductor gas sensors, I. Steady state gas response', Sensors and Actuators, 3, (1982/3), 233.
22. S. Kanefusa, M. Nitta and M. Haradome, 'Some unique aspects on $THO_2$—doped $SnO_2$ exposed to $H_2$ gas', J. Appl. Phys., 50(2), (1979), 1145.
23. S. Kanefusa and M. Haradome, 'Unique phenomena in $SnO_2$—based gas sensing devices exposed to ammonia gas', Solid State Electronics, 27(6), (1984), 533.
24. M. J. Fuller and M. E. Warwick, 'The catalytic oxidation of carbon monoxide on tin(IV) oxide', J. Catalysis, 29, (1973) 441.
25. M. Itch, H. Hattori and K. Tanabe, 'Catalytic sites on $SnO_2$ and $TiO_2$—$SnO_2$ for the isomerisation of 1-Butene', J. catalysis, 43, (1976), 192.

We claim:

1. A method for the production of tin oxide sensors containing Sb (III) as a dopant in oxide form, the method comprising mixing antimony bearing material with tin oxide powder and forming the sensor by depositing a slurry of the mixture onto a substrate and drying and sintering the slurry, the antimony bearing material being present in an amount sufficient to render the sensitivity of the sensor to one or more of the gases $H_2$, CO, or $CH_4$, substantially independent of the concentration of oxygen in the range $P_{O_2}$ $10^{-4}$–1 atm.

2. A method as claimed in claim 1 in which the antimony is in the form of antimony oxide powder.

3. A method as claimed in claim 2 in which the concentration of antimony is of the order of 2% w/w expressed as antimony oxide in the tin oxide.

4. A method of making a tin oxide gas sensor having a resistivity that at a measuring temperature increases with concentration of at least one gas to be measured, comprising the step of calcining the tin oxide in air at a temperature in excess of 1400° C., or otherwise heat treating the tin oxide so that it has a state of physical aggregation consistent with being formed by calcining in air at a temperature in excess of 1400° C.

5. A method as claimed in claim 4 in which the calcining temperature is approximately 1500° C.

6. A tin oxide gas sensor having a resistivity that at a measuring temperature increases with concentration of at least one gas to be measured, the sensor being made by the method of claim 4.

7. A tin oxide gas sensor comprising an inhomogeneous mixture of tin oxide and antimony in the form of Sb (III) as a dopant in oxide form.

8. A tin oxide gas sensor as claimed in claim 4 in which the concentration of antimony is of the order of 2% w/w expressed as antimony oxide in the tin oxide.

9. A tin oxide gas sensor as claimed in claim 8 in which at a second measuring temperature the resistivity of the sensor to said one gas decreases with increasing gas: concentration.

10. A tin oxide gas sensor as claimed in claim 6 in which the resistivity of the sensor is dependent on the concentration of several gases, the dependence at differing measuring temperatures being such that by measuring the resistivity of the sensor at several different measuring temperatures the composition of a gas to which the sensor is exposed may be calculated.

11. An array of tin oxide gas sensors mounted on a single substrate comprising a plurality of sensors as claimed in claim 6 with heater means to maintain the sensors at differing temperatures.

12. An array of sensors as claimed in claim 11 comprising additionally a sensor comprising an inhomogeneous mixture of tin oxide and antimony bearing material.

13. An array of sensors as claimed in claim 11 comprising additionally a linear-response hydrogen-selective tin oxide gas sensor incorporating bismuth.

* * * * *